US012608614B2

(12) United States Patent | (10) Patent No.: US 12,608,614 B2
Rahman et al. | (45) Date of Patent: Apr. 21, 2026

(54) GENERATING NEURAL NETWORKS TAILORED TO OPTIMIZE SPECIFIC MEDICAL IMAGE PROPERTIES USING NOVEL LOSS FUNCTIONS

(71) Applicants:GE Precision Healthcare LLC, Wauwatosa, WI (US); Purdue Research Foundation, West Lafayette, IN (US); University of Notre Dame du Lac, South Bend, IN (US)

(72) Inventors: Obaidullah Rahman, South Bend, IN (US); Madhuri Mahendra Nagare, Karmala (IN); Roman Melnyk, New Berlin, WI (US); Jie Tang, Merion Station, PA (US); Brian E Nett, Wauwatosa, WI (US); Charles Addison Bouman, West Lafayette, IN (US); Ken Sauer, South Bend, IN (US)

(73) Assignees: GE Precision Healthcare LLC, Waukesha, WI (US); Purdue Research Foundation, West Lafayette, IN (US); University of Notre Dame du Lac, South Bend, IN (US)

( * ) Notice: Subject to any disclaimer, the term of this patent is extended or adjusted under 35 U.S.C. 154(b) by 1001 days.

(21) Appl. No.: 17/804,224

(22) Filed: May 26, 2022

(65) Prior Publication Data

US 2023/0385643 A1 Nov. 30, 2023

(51) Int. Cl.
G06N 3/082 (2023.01)
G16H 30/40 (2018.01)
(52) U.S. Cl.
CPC ............. G06N 3/082 (2013.01); G16H 30/40 (2018.01)

(58) Field of Classification Search
None
See application file for complete search history.

(56) References Cited

U.S. PATENT DOCUMENTS 7,864,994 B2 1/2011 Fidrich et al.
11,126,914 B2 9/2021 Thibault et al.
(Continued)

OTHER PUBLICATIONS

Corda-D'Incan et al.. "Memory-Efficient Training for Fully Unrolled Deep Learned PET Image Reconstruction with Iteration-Dependent Targets", May 1, 2022, IEEE, IEEE transactions on radiation and plasma medical sciences, 6(5), 552-563 (Year: 2022).*
(Continued)

*Primary Examiner* — Davoud A Zand
(74) *Attorney, Agent, or Firm* — Amin, Turocy & Watson, LLP

(57) ABSTRACT

Techniques are described that facilitate generating neural network (NNs) tailored to optimize specific properties of medical images using novel loss functions. According to an embodiment, a system is provided that comprises a memory that stores computer executable components, and a processor that executes the computer executable components stored in the memory. The computer executable components comprise a training component that trains a NN to generate a modified version of computed tomography (CT) data comprising one or more optimized properties relative to the CT data using a loss function tailored to control learning adaptation of the NN based on error attributed to one or more defined components associated with the CT data, resulting in a trained NN, wherein the one or more defined components comprise at least one of a frequency component or a spatial feature component.

25 Claims, 15 Drawing Sheets

(56) References Cited

U.S. PATENT DOCUMENTS

| | | |
|---|---|---|
| 2018/0018757 A1 | 1/2018 | Suzuki |
| 2019/0325621 A1 | 10/2019 | Wang et al. |
| 2021/0150703 A1* | 5/2021 | Levanony .............. G16H 10/60 |
| 2021/0290191 A1* | 9/2021 | Qi ......................... A61B 6/5258 |
| 2022/0096055 A1* | 3/2022 | Di ......................... A61B 8/5207 |

OTHER PUBLICATIONS

Ananthabhotla, I. et al. | "Towards a Perceptual Loss: Using a Neural Network Codec Approximation as a Loss for Generative Audio Models". ACMM, Session 3C: Smart Applications, Oct. 21-25, 2019, Nice, France, 8 pages.

Yang, Q. et al. | "Low-Dose CT Image Denoising Using a Generative Adversarial Network With Wasserstein Distance and Perceptual Loss," IEEE Trans. Med. Imaging, vol. 37, No. 6, pp. 1348-1357, Jun. 2018, arXiv:1708.00961v2 [cs.CV] Apr. 24, 2018, 10 pages.

Yang, Q. et al. | "CT Image Denoising with Perceptive Deep Neural Networks". arXiv:1702.07019v1 [cs.CV] Feb. 22, 2017, 8 pages.

Ghani, M. U. et al. | "CNN based Sinogram Denoising for Low-Dose CT," in Imaging and Applied Optics 2018 (3D, AO, AIO, COSI, DH, IS, Lacsea, LS&C, Math, pcAOP), Jan. 2018, 3 pages.

Lee T-Ch. et al. | "Deep learning based adaptive filtering for projection data noise reduction in x-ray computed tomography". Proc. SPIE 11072, 15th International Meeting on Fully Three-Dimensional Image Reconstruction in Radiology and Nuclear Medicine, 110721D (May 28, 2019); doi: 10.1117/12.2534838, 6 pages.

Yuan, H. et al. | "SIPID: A deep learning framework for sinogram interpolation and image denoising in low-dose CT reconstruction". 2018 IEEE 15th International Symposium on Biomedical Imaging (ISBI 2018), Apr. 4-7, 2018, Washington, D.C., USA, 4 pages.

Rahman, O. et al. | "MBIR Training for a 2.5 D DL network in X-ray CT". 16th International Meeting on Fully Three-Dimensional Image Reconstruction in Radiology and Nuclear Medicine, Jul. 19-23, 2021, Leuven, Belgium, 3 pages.

* cited by examiner

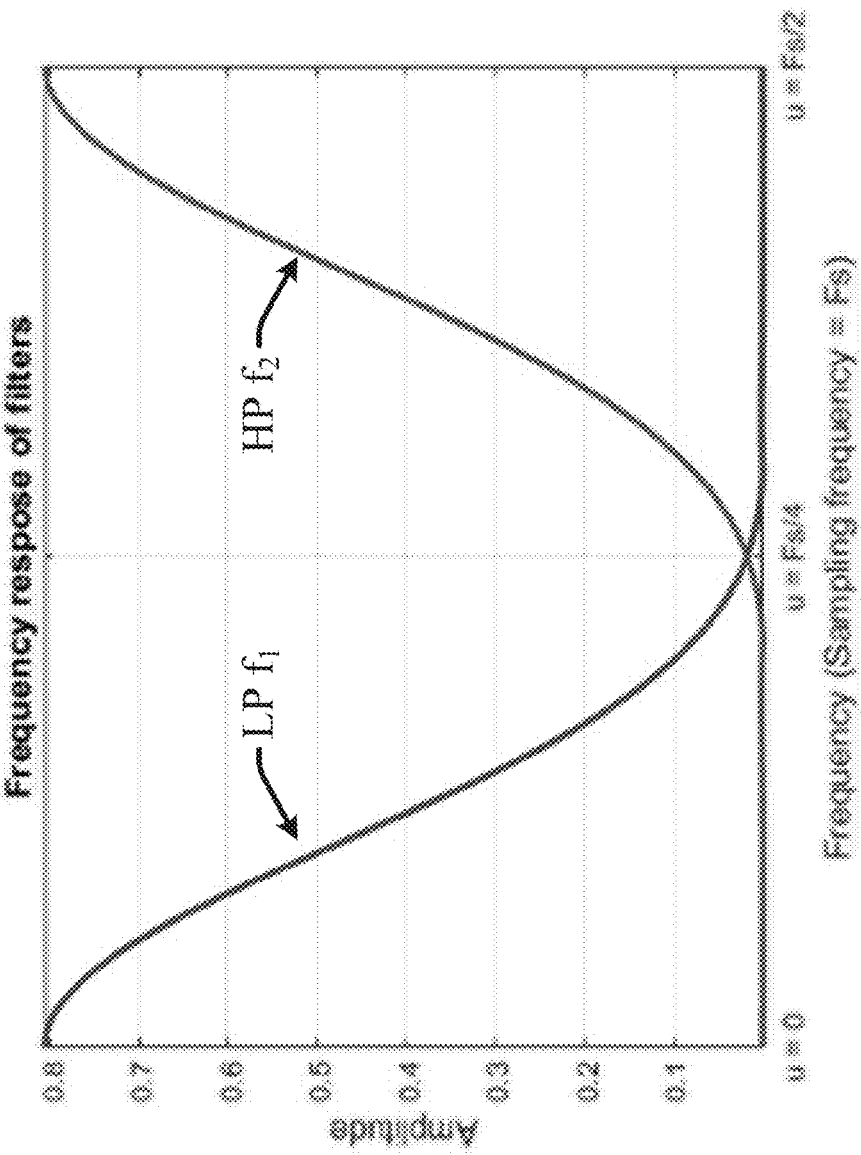
FIG. 5

| Flatness metric / entropy in bits of information | | | | | |
|---|---|---|---|---|---|
| Ideal case | Uncorrected | LP only ($\alpha = 0$) | LP + HP ($\alpha = 0.6$) | LP + HP ($\alpha = 0.8$) | LP + HP ($\alpha = 1$) |
| 8.0 | 7.76 | 7.07 | 7.46 | 7.89 | 7.86 |

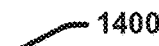

TRAINING, BY A SYSTEM COMPRISING A PROCESSOR, A NEURAL NETWORK TO GENERATE A MODIFIED VERSION OF COMPUTED TOMOGRAPHY DATA COMPRISING ONE OR MORE OPTIMIZED PROPERTIES RELATIVE TO THE COMPUTED TOMOGRAPHY DATA USING A LOSS ASSESSMENT MECHANISM TAILORED TO CONTROL LEARNING ADAPTATION OF THE NEURAL NETWORK BASED ON ERROR ATTRIBUTED TO ONE OR MORE DEFINED COMPONENTS ASSOCIATED WITH THE COMPUTED TOMOGRAPHY DATA, RESULTING IN A TRAINED NEURAL NETWORK

1402

APPLYING, BY THE SYSTEM, THE TRAINED NEURAL NETWORK TO NEW COMPUTED TOMOGRAPHY DATA TO GENERATE A NEW MODIFIED VERSION OF THE NEW COMPUTED TOMOGRAPHY DATA COMPRISING THE ONE OR MORE OPTIMIZED PROPERTIES

GENERATING NEURAL NETWORKS TAILORED TO OPTIMIZE SPECIFIC MEDICAL IMAGE PROPERTIES USING NOVEL LOSS FUNCTIONS

TECHNICAL FIELD

This application relates to applications of artificial intelligence (AI) in medical image processing and more particularly to generating neural networks tailored to optimize specific properties of medical images using novel loss functions.

BACKGROUND

Deep learning (DL) shows promise of advantages over conventional signal processing techniques in a variety of medical imaging applications. The networks' being trained from examples of data rather than explicitly designed allows them to learn signal and noise characteristics to most effectively construct a mapping from corrupted data to higher quality representations. In inverse problems, one has options of applying DL in the domain of the originally captured data, in the transformed domain of the desired final representation, or both.

Computed tomography (CT), one of the most valuable tools in medical diagnostics, is already being improved by DL methods. However, as CT X-ray dosages have been reduced to protect patients' long-term health, the quality of diagnostic CT imagery can be limited. In addition to common photon counting noise, low-signal artifacts such as local image bias and streaks may interfere with diagnostics. DL networks are a powerful tool in reducing the severity of these effects, whether for removal of common quantum noise resulting from the Poisson-distributed photon counts, or for reduction of the ill effects of metal implants on image quality.

However, the subjective and objective qualities of the resulting images are not always aligned with the needs and preferences of radiologists. Using conventional training for the networks is often a hit-or-miss process in which extensive training on large image ensembles is necessary. Although, the selection of training data is driven quite directly by the corruption on which the focus lies, the way in which differences between the target signal and the neural network output is penalized in training generally follows conventional, pointwise loss functions. Furthermore, a change in CT protocol or imaging technology may require an entirely new training sequence. The field needs greater quantification and control of the adjustments in the CT images that the networks are to perform in the inference stage.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described that facilitate generating neural networks tailored to optimize specific medical image properties using novel loss functions. Various embodiments are directed to processing CT image data; however, the disclosed techniques may be extended to other medical image modalities.

According to an embodiment, a system is provided that comprises a memory that stores computer executable components, and a processor that executes the computer executable components stored in the memory. The computer executable components comprise a training component that trains a neural network to generate a modified version of CT data comprising one or more optimized properties relative to the CT data using a loss function tailored to control learning adaptation of the neural network based on error attributed to one or more defined components associated with the CT data, resulting in a trained neural network. The one or more defined components can comprise a frequency component, a visual feature component, and/or a spatial feature component. In some implementations, the CT data comprises sinogram data for a CT image and the modified version comprises modified sinogram data for the CT image. In other implementations, CT data comprises a CT image and the modified version comprises a reconstructed CT image.

In various embodiments, the computer executable components further comprise an inferencing component that applies the trained neural network to new CT data to generate a new modified version of the new CT data comprising the one or more optimized properties. In some implementations of these embodiments, the computed tomography data comprises sinogram data for a CT image, the modified version comprises modified sinogram data for the CT image, the new CT data comprises new sinogram data for a new CT image, the new modified version comprises new modified sinogram data for the new CT image, and wherein the computer executable components further comprise a reconstruction component that generates a reconstructed version of the new CT image using the new modified sinogram data (e.g., as a filtered back projection (FBP) image or the like).

In some embodiments in which the one or more defined components comprise the frequency component, the loss function can weight the error of as a function of the frequency component. With these embodiments, the loss function can penalize removal of configurable frequencies and frequency ranges from the input image.

In some implementations, the loss function utilizes spatial filtering of a difference between input data of the neural network and a target data set as input to the loss function. Additionally, or alternatively, the loss function can apply a penalty to a difference between input data and output data of the neural network. In some implementations of these embodiments, the loss function assesses the penalty after spatial filtering of the difference. In other implementations, wherein the one or more defined components comprise the spatial feature component, the training component can employ a spatial feature extraction step to furnish a mask to assess the penalty on the difference. Still in other embodiments, the loss function can use a composite of differences among three or more signals as input to generate a training penalty.

In some embodiments, elements described in connection with the disclosed systems can be embodied in different forms such as a computer-implemented method, a computer program product, or another form.

DESCRIPTION OF THE DRAWINGS

FIG. 5 presents a graph illustrating the frequency response of low and high pass filters used to control error content of CT images in association with training a NN in the sinogram domain.

FIG. 14 illustrates a block diagram of an example, non-limiting computer implemented method for CT image reconstruction that employs a NN to control error localized in frequency and/or spatial content in accordance with one or more embodiments of the disclosed subject matter.

DETAILED DESCRIPTION

Figure 1:
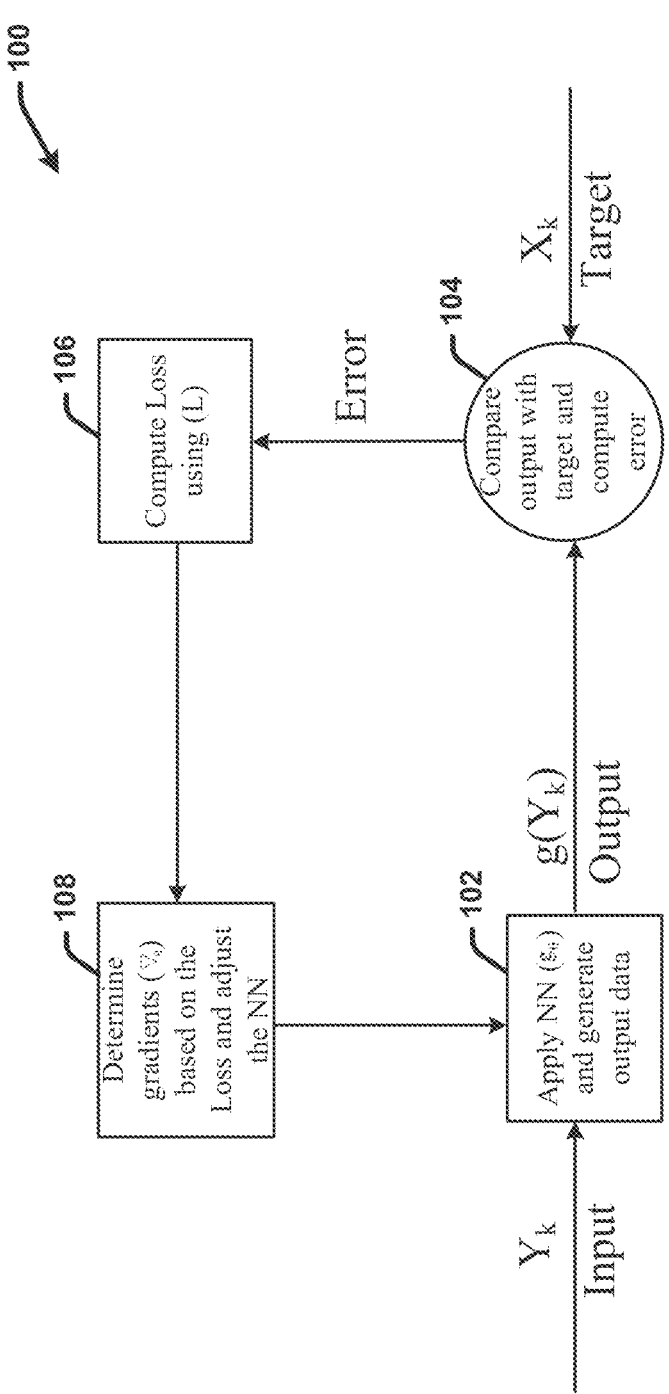
FIG. 1 illustrates a high-level flow diagram of an example process for training a neural network (NN) in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to techniques that facilitate generating neural networks tailored to optimize specific medical image properties using novel loss functions. The main challenge the disclosed techniques proactively address is the development of neural network models that favor medical image reconstruction characteristics that are not well described by norms such as mean-squared error (MSE) or mean-absolute error. Particularly in the field such as X-ray and CT, where radiologists' subjective preferences in image characteristics are key to acceptance, the disclosed techniques provide for training image transformation networks that penalize differences in DL more creatively. These penalties may be applied in the raw data domain, such as the X-ray/CT sinogram, and/or in the image domain.

Various embodiments are directed to the design and usage of DL loss functions with a focus on spectral, spatial or other specific properties of error that will give the system operator greater flexibility in tailoring an artificial neural network (ANN) to specific applications. In some embodiments, the DL loss functions can be tailored to shape both the frequency content of the signal and preservation of boundary information of particularly significant structures in diagnostic images (e.g., detailed structures such as vessels, lesions, and other target structures). For example, in medical CT imaging, the preferences of radiologists for certain types of noise texture can be accommodated with a network tuned to penalize parts of the noise power spectrum (NPS) differentially. With the disclosed techniques, a DL selection could be offered similar to the current "soft," "bone," etc. filter kernels with much greater variety than simple cutoff frequencies. In this regard, the general tendency of DL networks trained with conventional MSE loss functions is to oversmooth the data. The disclosed techniques can mitigate such oversmoothing with loss functions that penalize the removal of selected frequencies or frequency ranges in the error power spectrum. In addition, the disclosed techniques can employ adaptive spatial weighting of the error in the loss function which allows focus of DL training and inference on low dose areas in signal correction, as well as using feedback of structure in the error residual to improve training.

To facilitate this end, the disclosed subject matter provides systems and methods that facilitate training and developing neural networks tailored to optimize specific medical image properties. Various embodiments are directed to CT imaging; however, one or more aspects of the disclosed subject matter may be extended to other medical images modalities. For example, the types of medical image data that may be processed and optimized using the disclosed techniques can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MM) images, ultrasound (US) images, color flow doppler (CD) images, position emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques.

The medical imaging processing models disclosed herein can also be configured to process 3D images.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a high-level flow diagram of an example NN training process 100 in accordance with one or more embodiments of the disclosed subject matter. Process 100 corresponds to high-level deep learning process for training a NN to transform an input data signal, into an ideal form using a target data set.

In this regard, deep learning is a part of a broader family of machine learning methods based on ANNs with representation learning. The learning/training of such networks may be supervised, semi-supervised and/or unsupervised. As applied to medical imaging optimization, DL has been used to train NNs to remove corruption from medical image data by training the network to transform input medical image data into an ideal form of that medical image data from ground truth (GT) examples rather than explicitly designed, a supervised learning regime. This allows them to learn signal and noise characteristics to most effectively construct a mapping from corrupted data to higher quality representations. This is usually accomplished by presenting many pairs of good and bad images and teaching the NN how to map from a corrupted image into the good image such that the network learns how to make the input match the target.

During training, the NN is designed by processing a corrupted input image and adjusting strengths of interconnections among artificial neurons with the goal of making the network's output, on the average, as close as possible to the ideal form of the image. This ideal form may be well known in training phase of the NN, in which one may start with a perfect signal as the "target" and then corrupt it according to the character of noises and artifacts typically encountered in application. Alternatively, the target image may be imperfect, but far less afflicted with error than those encountered as measurements.

In accordance with process 100, $Y_k$ corresponds to the input data signal, $g(Y_k)$ corresponds to the output signal, and $X_k$ corresponds to the target data signal. The subscript k is used herein to denote the indices of training data pairs (e.g., k may be 1, 2, 3, etc.). The number of input data samples and target data samples can vary. For instance, in some implementations, several (e.g., all, some, etc.) of the input data samples may be paired with a single "ideal" target data sample. In other implementations, each input data sample may be paired with a separate target data sample.

As applied to the disclosed medical imaging optimization techniques, the input data signal $Y_k$ can correspond to corrupted medical image data (e.g., corrupted raw CT sinogram data and/or corrupted CT image data) and $X_k$ corresponds to the target medical image data that the network is trying to transform the input image data into. At 102, the NN is applied to $Y_k$ to generate the "improved" output image data $g(Y_k)$. At 104, the output image data is compared with the target $X_k$ to compute or determine a measurement of error between them that represents a difference between $g(Y_k)$ and $X_k$. At 106, a loss function (L) is utilized to compute some average measure of loss or penalty to be applied to the network based on the error. In this regard, parameters governing the NN behavior are denoted by θ, and L corresponds to a loss function that penalizes a measure of error data between an ensemble of network-processed input data and their respective targets $X_k$ determined at 104. The gradient of the loss function's penalization of the error, as a function of θ, is used to improve the averaged match between target and output of network during training.

At 108, this loss is used to determine gradients to correct the network attributes, such as NN node coefficients, NN node interconnections, or other representations of neural interconnections that reduce or minimize the loss, and the NN is adjusted accordingly. This process 100 is iteratively performed for the input training data until convergence is reached and/or an acceptable level of loss is reached. In this regard, simple multiplicative coefficients or other representations of neural interconnections are iteratively adjusted to minimize some average measured error, or loss, between an ensemble of network-processed input data and their respective target counterparts. The measured loss is backpropagated through the NN at 108 to provide gradients to correct the connections and reduce loss, thus "learning" the inverse operator. Following training/convergence, the trained NN may be applied to new data sets in order to reduce their content of error as described by the loss function used during the training process 100.

A common loss function used at 106 for penalizing the error in NN training processes such as process 100 has been the mean-squared error (MSE). Expressed mathematically, let us define Y as the input data, which we model as a function of some ideal, target image X (i.e., Y=h(X)). The task of the NN (g) is to extract from Y a rendering close to the unknown, ideal image (or sinogram depending on the data being processed by the NN). If we define $g=h^{-1}$, the NN training process would seek to train g (i.e., the NN) to produce X=g(Y). Equality is seldom achievable due to noise or other corruption, and we optimize in the sense of average, possibly weighted, error. If we use the variable k to index among training pairs, n to index entries in vectors $X_k$ and $Y_k$, and θ to represent the variable parameters of the NN, our DL-trained mapping $g_\theta$ using average MSE for the loss function L case may be expressed in terms of Equation 1, in which the weightings $w_{k,n}$ may be fixed in either or both variables, or may be adapted according to relative local characteristics of data.

$$\hat{\theta} = \underset{\theta}{\arg\min} \sum_{k,n} w_{k,n} [X_{k,n} - (g_\theta(Y_k))_n]^2. \qquad \text{Equation 1}$$

This weighted, mean-squared penalty on the standard error $S_k \triangleq X_k - g_\theta(Y_k)$ has a number of potential advantages, including being statistically well-matched to Gaussian noise. In cases where less severe penalization of large errors is desired, squared error may be replaced by absolute error, similarly to penalty adjustment in edge-preserving regularization.

However, while simple norms such as expressed above provide highly useful loss metrics, it has long been recognized in the image processing community that they are inaccurate for applications in which the final receiver for the system's output is a human observer. In this regard, the training that results from process 100 in which differences between the target signal and the measured data are penalized using conventional, pointwise loss functions such as MSE, or weighted MSE (as expressed in Equation 1) tends to overemphasize certain characteristics and present new problems in the output image. For example, when the training is performed with a perfectly clean target image with input images that are corrupted or noisy, the MSE loss function typically results in the network flattening the output image. The output image may contain less noise, yet it loses some high frequencies because the loss function that it learned to optimize didn't tell it to preserve certain things, it was just concerned with matching the respective images in the terms of total MSE as best it could. For diagnostic CT imaging, in which much analysis is performed by radiologists, more subjective quality metrics are applied by the end users of the technology, and spectral content of residual noise, plateauing of image levels in low-contrast areas, and other context-dependent evaluations must be addressed.

With this problem in mind, the disclosed subject matter provides new techniques for penalizing the errors made in the inverse operation to train the NN to preserve or remove specific components of the input image data as desired. As applied to CT images, such components may include one or more defined frequency components (e.g., specific frequencies and/or frequency ranges extracted from CT sinogram data), one or more defined visual feature components (e.g., visual image features in the image domain, such as specific objects, visual image properties (e.g., brightness, hue, patterns, boundary lines, artifacts, etc.), one or more defined spatial feature components (e.g., variables localized in the spatial domain), and other configurable features in the image domain and/or the raw data domain. In this regard, CT image data comprises a spatial component because CT images are generated from a three-dimensional (3D) data set of projection signals captured at different 3D positions relative to the patient. Each CT image corresponds to a slice of a patient's anatomy with image variables (or features or components) that are spatially aligned in a 3D space (i.e., an (x, y, z) Cartesian space). Reference to the frequency component of the data refers to variables indexing frequency of oscillation in the 3D space (i.e., the (x,y,z) space), through the Fourier transform. In this regard, frequency variables or components as well as visual feature variables or components of CT image data can have a spatial component that refers to its relative location in the 3D space. Thus, both frequency components and visual feature components may be spatially filtered in some embodiments, as described in greater detail below.

The goal is to train the NN in such a way that it will be more selective in what it learns and what sorts of things it emphasizes. To facilitate this end, the disclosed subject matter provides novel loss metrics which may expand the usefulness of DL in CT and other medical imaging modalities. In various embodiments, the sense of optimality can be generally represented by Equation 2, where L is now a function that may capture any number of spatial characteristics in the error.

$$\hat{\theta} = \operatorname*{argmin}_{\theta} \sum_k L[X_k, Y_k, g_\theta(Y_k)]. \qquad \text{Equation 2}$$

In this regard, as applied to process 100, in one or more embodiments, the loss function L as represented in Equation 2 can be used at 206 to selectively control how the error is penalized based on specific components of the error as opposed to generally penalizing the total difference between the NN output image and the target. In this regard, the loss function employed by the disclosed techniques can be tailored to control learning adaptation of the NN based on error attributed to one or more defined components or a defined subset of variables associated with the input data and/or the output data. In the CT arena, the NN can be configured to improve the input signal in the sinogram domain, where measurements are made directly, and/or in the image domain after reconstruction by any existing CT image reconstruction algorithm. The signal and error statistics in these two differ, leading to designs tailored for each case, as described in greater detail below. It is noted that Equation 2 has three arguments and uses a composite of differences among three or more signals as input to the training penalty, wherein at least one of the three or more signals can comprise an "Error" content signal based on error calculated using one or more of the techniques described below. However, these three arguments are not limited to "Error" signals and can exploit any relationship among the input signals.

Figure 2:
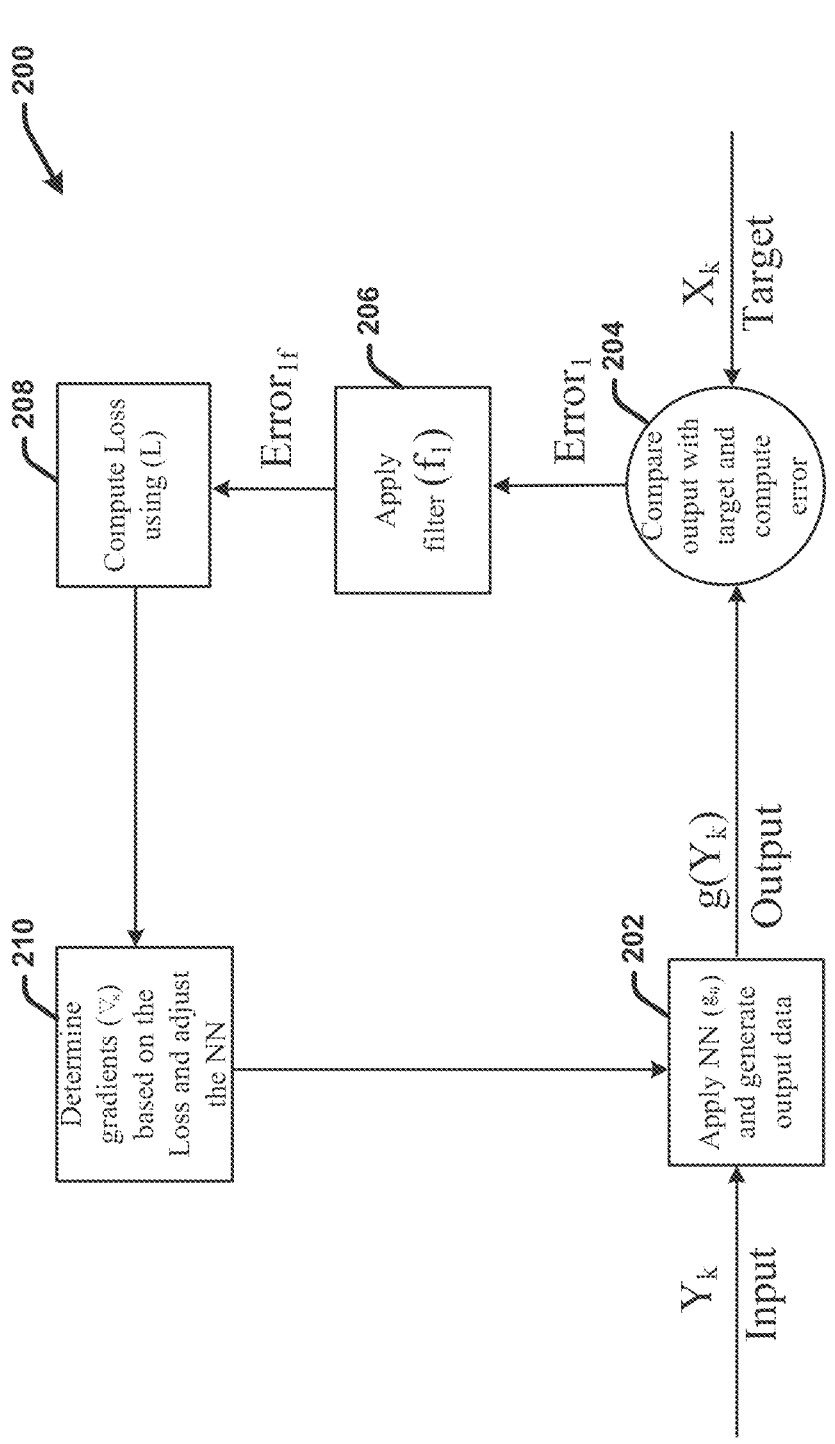
FIG. 2 illustrates a high-level flow diagram of an example training process for training a NN to control error content using filtering of the difference between the training output data and a target data set in accordance with one or more embodiments of the disclosed subject matter.

FIG. 2 illustrates a high-level flow diagram of an example training process 200 for training a NN to control error content using filtering of the difference between the training output data and a target data set in accordance with one or more embodiments of the disclosed subject matter. Process 200 is similar to process 100 with the addition of a filtering step at 206. Repetitive description of like elements employed in respective embodiment is omitted for sake of brevity.

In accordance with process 200, the filter $f_1$ corresponds to a filter that may be applied to the error content ($\text{Error}_1$) that represents the difference between the NN output data $g(Y_k)$ and the target data $X_k$ (or target dataset). In this regard, at 204, the output data is compared to the target data to generate a measure of ($\text{Error}_1$) that represents the difference between the two. Such difference represents an "error" in that any difference between the output and the target is considered undesirable (e.g., whatever is different between the target and the output is undesirable in the sense that the output should match the target). At 206, the error data ($\text{Error}_1$) is filtered using $f_1$ to remove select content from the error data that the system operator/designer does not want the NN to penalize when evaluating the loss at 208. The filtering at 206 results in the generation of filtered error content ($\text{Error}_{1f}$) that removes one or more components of the error that would have been otherwise penalized at 208. Process 200 further proceeds in accordance with process 100, wherein at 208, the loss is computed using a suitable loss function that determines and applies a penalty (i.e., computes the loss) based on the filtered error content ($\text{Error}_{1f}$). The specific loss function L used at 208 can include MSE, absolute MSE or another type of loss function. At 210, the system (e.g., the computing system performing the training processes, an example of which is presented in FIG. 13) further determines the gradients based on the loss and adjusts the NN accordingly.

The specific filter applied at 206 can vary depending on the type of the input and output data, associated error content, and desired characteristics of the error content that the system operator/designer would like the NN to emphasize penalizing or not. In various embodiments as applied to CT image optimization, filter $f_1$ can be a filter that may be applied to sinogram CT data to selectively filter the error content ($\text{Error}_1$) based on frequency to selectively remove specific frequencies or frequency ranges represented in the error content. In this regard, conventional, point-wise MSE alone as loss may be thought of as a flat spectral penalty. In some cases, the system operator/designer may desire to focus on removing artifacts with low or medium spatial frequency content, while in other cases the system operator/ designer may desire to focus removing artifacts with high spatial frequency content. Accordingly, penalizing all frequencies equally may be counter-productive. In accordance with these examples, the $f_1$ filter can be tailored to filter the error content to remove components with frequencies that the network operator/designer does not want the loss function to penalize. With these embodiments, with reference to FIGS. 1 and 2, the loss function (L) applied at 106 in process 100 can take the form of Equation 3, wherein φ is a suitable error metric applied only according to the passband filter f (i.e., f=$f_1$) and wherein $S_k$ represents the pre-filtered error content (i.e., $S_k$=Error$_1$ in process 200).

$$L[S_k] \triangleq \varphi[f(S_k)] \qquad \text{Equation 3.}$$

For example, in some implementations in which the system operator/designer wants to train the NN to focus signal correction on removing errors in lower frequencies (and not high frequencies), the system operator/designer can configure the filter f as a lowpass (LP) filter that removes frequency content of the error—that exceeds a defined low frequency threshold. With these implementations, the higher frequency error becomes a "don't care" element for the network. Alternatively, band-pass or high-pass filtering may be used to focus loss on those medium or high portions of the error spectrum. For example, the system operator/designer can configure the filter f as a high-pass (HP) filter that removes frequency content of the error $S_k$ that is lower than a defined mid or high frequency threshold. Furthermore, particularly in three-dimensional image vectors, frequencies may be treated differently along the three axes (e.g., axial, sagittal, coronal, for CT images or another set of defined axes). For example, different filters (e.g., LP and HP) and/or thresholds may be used for different directional vectors.

The discussion above is most commonly addressed to conventional CT imagery in two or three dimensions, in which spatial frequency has roughly equivalent meaning in all dimensions. However, the present methods are intended at least as importantly for use in the native domain of the data, the sinogram. Application of the type of loss function in Equation 3 in the sinogram requires modeling behavior in such coordinates as row, channel and view, where the first two index in the detector panel of the CT gantry, and the last indexes the distinct rotating, two-dimensional views of patient or object. In this case, the error filtering operation of f can be spatially adapted based on spatial coordinates of respective projections represented in the sinogram data, as statistics of both the underlying signal and the corrupting noise vary spatially in the sinogram domain. Thus, in one or more embodiments, as applied to CT sinogram data, the filtering processes applied by the filter f (or $f_1$) comprises a spatial filtering process.

In this regard, with reference to process 200, in some embodiments, the input data $Y_k$ can comprise raw sinogram CT data that can be used to generate corresponding CT images. The raw sinogram CT data can include one-dimensional (1D), two-dimensional (2D), and/or three-dimensional data (3D) (e.g., different views). The training process 200 involves training the NN at 202 to generate optimized sinogram data as output data $g(Y_k)$ using one or more target exemplars ($X_k$) (or a target dataset in implementations in which the input data comprises 2D or 3D data) corresponding to ideal representations of the sinogram data. At 204, the output sinogram data is compared to the target sinogram data to generate a measure of (Error$_1$) that represents the difference between the two. For example, the (Error$_1$) may comprise a vector or vectors that represent the difference in frequency content between the output sinogram data and the target sinogram data in one or more directions. At 208, the error data (Error$_1$) is filtered using a filter ($f_1$) to remove select frequencies or frequency ranges from the error content that the system operator/designer does not want the NN to penalize when evaluating the loss at 208, resulting in filtered error content (Error$_{1f}$). As noted above, in some implementations, different filters (e.g., LP and/or HP) and/or thresholds may be used for different spatial directions. Process 200 further proceeds in accordance with process 100, wherein at 208, the loss is computed using a suitable loss function that determines and applies a penalty (i.e., computes the loss) based on the filtered error content (Error$_{1f}$). The specific loss function used at 208 can include MSE, absolute MSE or another type of loss function. At 210, the system further determines the gradients based on the lass and adjusts the NN accordingly.

Process 200 (and/or Equation 3) as applied to filtering the error content for CT sinogram data based on frequency content of the error between the NN output and the target data is referred to herein as "spectral loss shaping." Preliminary testing of the above-described aspects of spectral loss shaping on phantom and clinical data revealed that some types of low-signal noise in CT data are most effectively removed from the sinogram, where they have relatively little spatial correlation. When backprojected during image reconstruction, these high-variance measurements may appear as streaks at the angles of the respective projections, and their strong spatial correlation in that direction may make them relatively difficult to suppress with filtering in the image. A NN network may be trained in accordance with process 200 using a LP filter to eliminate much of this noise from the sinogram using conventional loss metrics at 208 such as MSE; however, training with conventional loss metrics (e.g., MSE) in the sinogram at 208 does not weight error according to the damage done to the final image achieved by filtered backprojection (FBP) reconstruction. For example, the spatial filtering off (or $f_1$) converts a projection P(β, ω) parameterized by orientation β and spatial frequency ω in the channel direction according to |ω|P(β, ω) or an apodized version of this "ramp" filter. It is this high-frequency boosted projection that will be added to the final image during reconstruction.

In some embodiments, to more properly penalize the projection error, the loss function L applied at 208 can comprise an optimized loss function as defined by Equation 4 wherein f is a windowed version of the inverse Fourier transform of |ω|, and convolution is performed in the channel direction.

$$\hat{\theta} = \operatorname*{argmin}_{\theta} \sum_{k,n} w_{k,n} [f * (X_{k,n} - g_\theta(Y_k)_n)]^2. \qquad \text{Equation 4}$$

Figure 3:
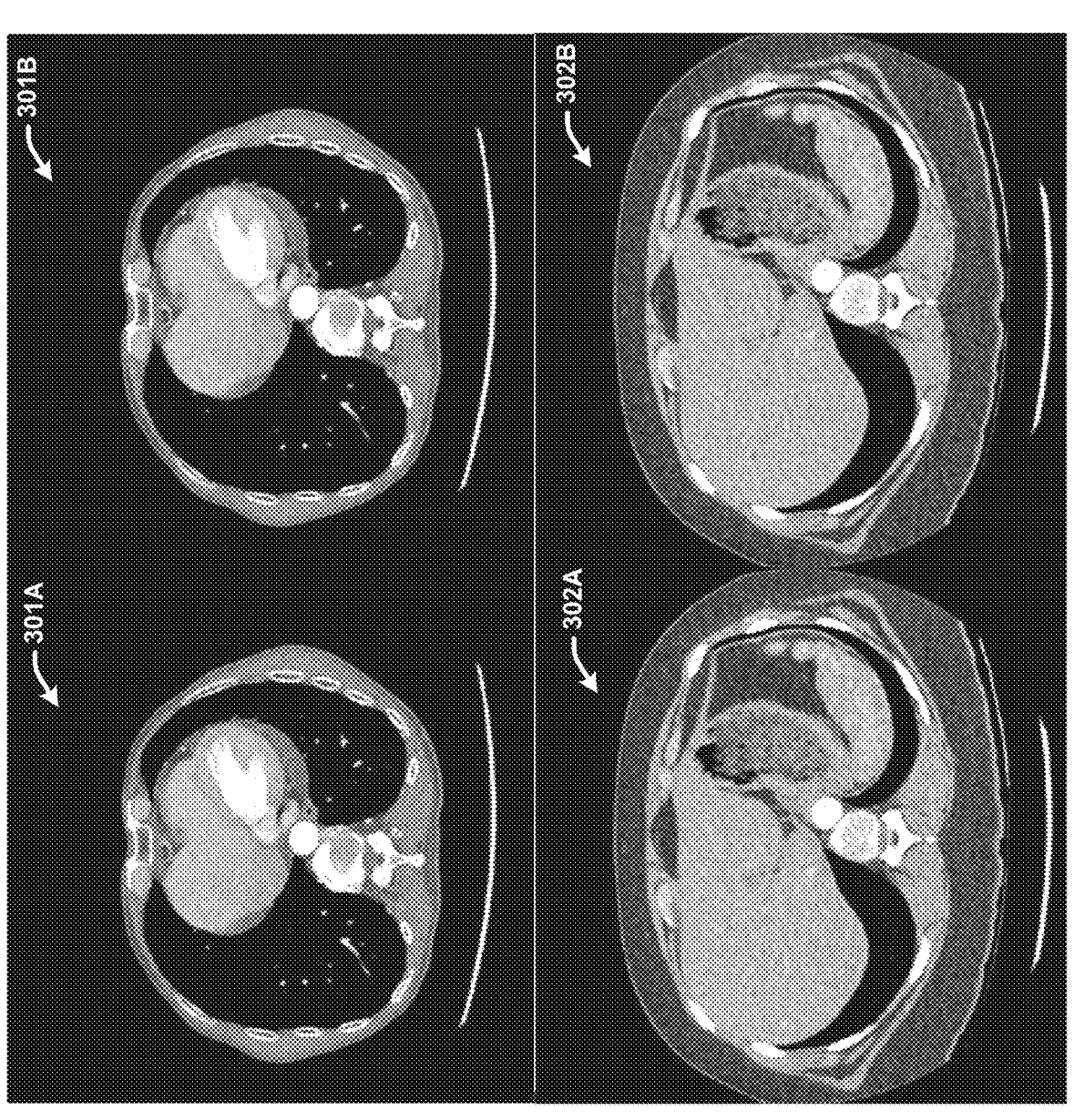
FIG. 3 presents example CT images before and after optimizing using a NN trained to control frequency content in the sinogram domain using a high pass (HP) filter to emphasize sources of streaks in reconstructed images.

FIG. 3 presents example CT images before and after spectral loss shaping using a NN trained to control frequency content in the sinogram domain using a HP spatial filter in accordance with process 200 and using Equation 4 for the loss function (L) at 208 with "ramp" filter loss. Images 301A and 301B respectively comprise CT images depicting the chest including the heart and images 302A and 302B respective comprise CT images of the liver and stomach area. All four images were reconstructed from sinogram data using standard FBP reconstruction. The respective (left) images 301A and 302A correspond to CT images generated from sinogram data processed by the NN trained with conventional MSE loss, and the (right) images 301B and 302B correspond to CT images generated from the NN processed sinogram data (i.e., the optimized sinogram data) after training with ramp filter emphasis. The NN training data consisted of a high-dosage sinogram of a chest phantom as the target data $X_k$, with synthesized Poisson and electronic noise added to form the input data $Y_k$. In the clinical images generated from the optimized sinogram data (i.e., images 301B and 302B), there is observable improvement in the suppression of noise streaks resulting from heavier attenuation of rays traversing the spine, without compromising the anatomical details, demonstrating the efficacy of the disclosed spectral loss shaping techniques using LP filtering.

Figure 4:
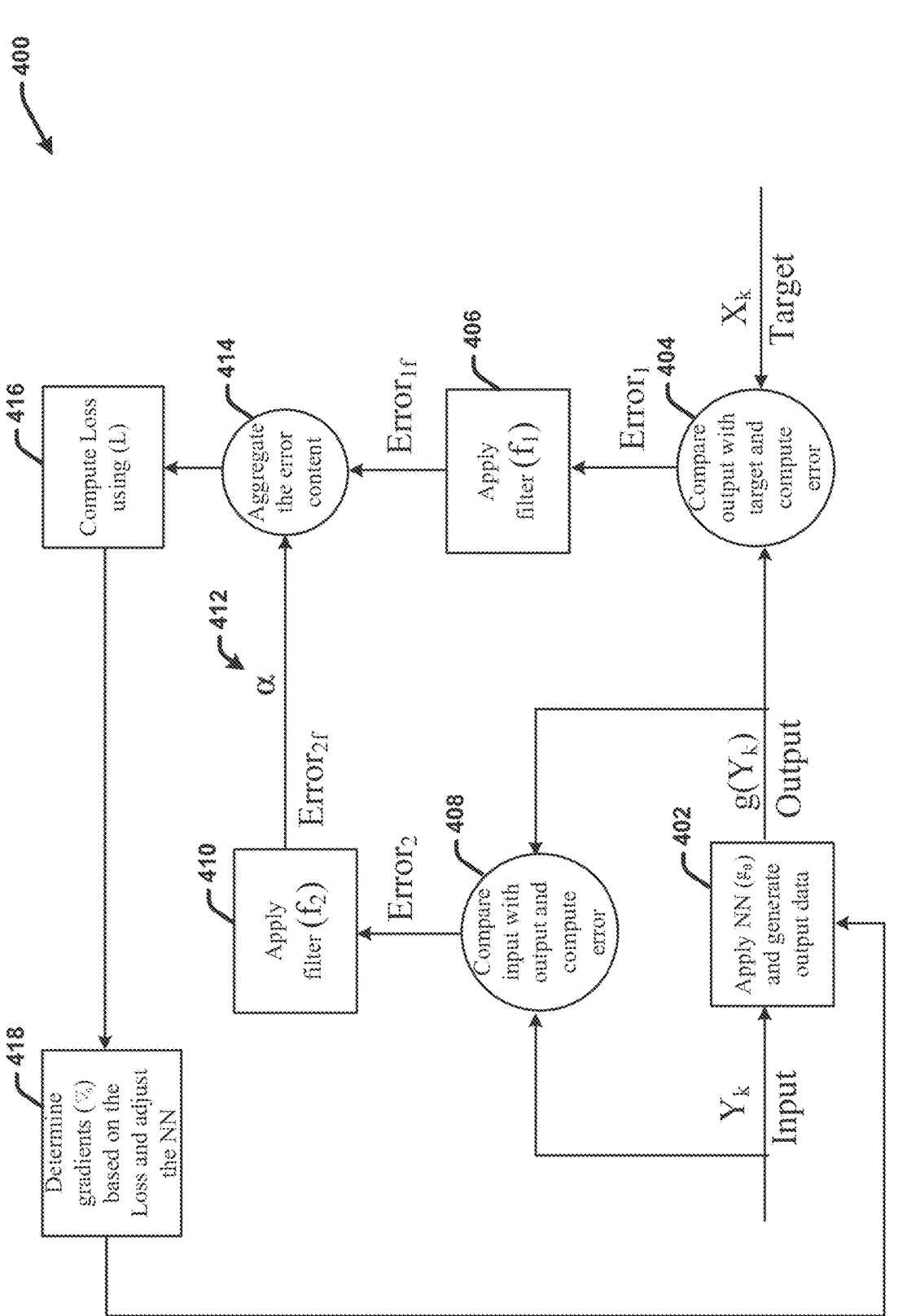
FIG. 4 illustrates a high-level flow diagram of an example training process for training a NN to control error content using both filtering of the difference between the training input data and output data, and filtering of the difference between target and output, in accordance with one or more embodiments of the disclosed subject matter.

FIG. 4 illustrates a high-level flow diagram of an example training process 400 for training a NN to control error content using filtering of the difference between the training input data and output data in accordance with one or more embodiments of the disclosed subject matter. Process 400 is similar to process 200 with the addition of a second filtering step at 410 using a second filter $f_2$. In this regard, processing steps 402, 404 and 406 respectively correspond processing steps 202, 204 and 206 described with reference to process 200. Repetitive description of like elements employed in respective embodiment is omitted for sake of brevity.

In accordance with process 400, the second filter $f_2$ corresponds to filter that may be applied to filter error content (Error$_2$) that represents the difference between the NN input data $Y_k$ and output data $g(Y_k)$. In this regard, at 408, the output data is compared to the input data to generate a measure of (Error$_2$) that represents the difference between the two. This difference or error content corresponds to the data content that the NN removed from the input data. In some embodiments, the system operator/designer may want to train the NN to not remove select content from the input data (e.g., select frequencies or frequency ranges, select image features/objects, etc.). With these embodiments, the second filtering step at 410 may be used to filter the error content to identify those components/features of the error content (Error$_2$) that the NN removed from the input data that the NN operator/designer does not want removed. In this regard, the second filter $f_2$ can filter the error content to remove all other components from the error content that the NN should remove, resulting in second filtered error content (Error$_{2f}$) that contains the select components/features whose removal from the input is undesired. This type of filtered error content can be processed by the loss function applied to train the NN to penalize the removal of such content, and thus train the NN to preserve selected content. To this end, the second filtering mechanism presented in process 400 is referred to herein as "perseveration of selected error content." In accordance with process 400, this second filtered error content (Error$_2$f) may (optionally) be weighted using a configurable weighting factor ($\alpha$) at 412 to increase or decrease its penalty value in the loss function. At 414 the first and second error signals filtered error signals (e.g., (Error$_{1f}$ and Error$_{2f}$ or $\alpha$Error$_{2f}$) can be aggregated or combined as input to the loss function computed at 416. In this regard, at 416, the loss is computed using a suitable loss function that determines and applies a penalty (i.e., computes the loss) based on the aggregated filtered error content. The specific loss function L used at 416 can include MSE, absolute MSE or another type of loss function. At 418, the system (e.g., the computing system performing the training processes, an example of which is presented in FIG. 13) further determines the gradients based on the loss and adjusts the NN accordingly.

The specific second filter $f_2$ applied at 208 can vary depending on the type of the input and output data, associated error content, and desired characteristics of the removed error content (Error$_2$) that the system operator/designer would like the NN to emphasize penalizing or not. In some embodiments as applied to CT image optimization, filter $f_2$ can comprise a filter that may be applied to sinogram CT data to selectively filter the error content (Error$_2$) based on frequency to selectively penalize removal of specific frequencies or frequency ranges represented in the error content (Error$_2$).

In this regard, the spectral loss shaping techniques described with reference to FIGS. 2 and 3 represented any unpenalized portion of the CT sinogram frequency spectrum as a "don't care" component for the loss. However, often times, the inverse operation of the NN mapping of the input sinogram to the target tends to result in the elimination of high frequencies in the output data, and this may occur even when the penalized loss is restricted to low frequency error using a LP filter at 406. An example application is using DL for low signal correction in CT images, where some of the most problematic artifacts are of low to medium spatial frequency. Here it may be advantageous to retain parts of the error frequency spectrum in the output data when the NN is applied in the sinogram domain. Powerful, adaptive denoisers in the image domain can capitalize on the relatively stationary underlying image statistics to remove higher frequency noise with little damage to edge resolution. Thus, the second filtering mechanism in process 400 can be used to actively discourage suppression of this part of the error signal in the first stage of processing.

In accordance with these embodiments, the loss function L applied at 416 can comprise a loss function that penalizes the removal of components of the signal $Y_k$ according to spectral content (e.g., as applied to CT sinogram data), or other information in separate embodiments (e.g., specific image features, structures, etc., as described in greater detail with reference to FIGS. 8-12). The components of the error content (i.e., Error$_2$) can be categorized and penalized by location in space and/or frequency. This component of the loss may be expressed similarly to Equation 3, but with the argument redefined in accordance with Equations 5 and 6, wherein $T_k$ represents the error content corresponding to the difference between the input and output signals (i.e., Error$_2$).

$$T_k \triangleq Y_k - g_\theta(Y_k) \qquad \text{Equation 5}$$

$$L[S_k, T_k] \triangleq \varphi[f_1(S_k) + \alpha f_2(T_k)] \qquad \text{Equation 6.}$$

In this regard, as applied to process 400 and training the NN ($g_\theta$) to correct CT sinogram data, wherein the first filter $f_1$ penalizes a first portion of the spatial frequency spectrum, in some embodiments, the second filter $f_2$ can penalize a second, different portion of the spatial frequency spectrum of the error. For example, in some implementations, the first filter $f_1$ can comprise a LP filter and the second $f_2$ filter can comprise a HP filter that extracts the high frequency content from the Error$_2$ content and includes it in the filtered Error$_{2f}$ content. With these embodiments, the two types of error signals can be combined at 414 before the application of the norm Ø and the gradient for backpropagation at 416 and 418. The weighting factor $\alpha$ can also optionally be applied to the filtered Error$_{2f}$ content at 412 according to the frequency content of the error. The weighting factor $\alpha$ can be any positive value, with increase resulting in more of the desired frequency components preserved in the output. In this regard, as applied to preserving high frequency content, as the weighting factor $\alpha$ increases, the removal of the high frequency content is penalized more, resulting in training the neural network to more strongly preserve the high frequency content.

Figure 6:
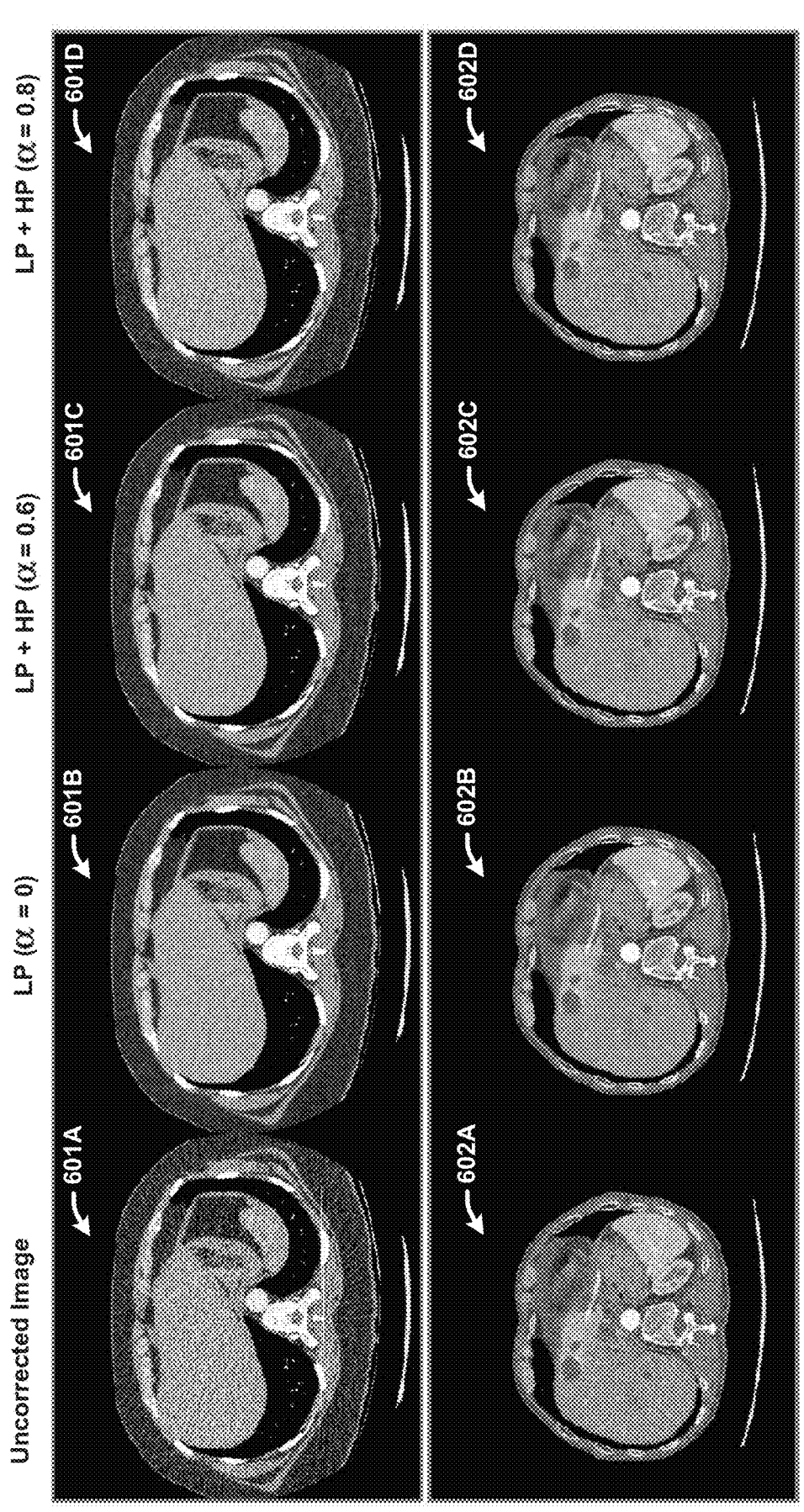
FIG. 6 presents example CT images before and after optimizing using a NN trained to control frequency content in the sinogram domain with different low pass (LP) and high pass (HP) filter combinations.

Preliminary testing of the above-described embodiment of process 400 as applied to CT sinogram data was also performed on phantom and clinical data. In this setup, the training loss was calculated as a function of the weighted sum of LP filtered error between output and target sinograms, and HP filtered error between input and output sinograms (e.g., $f_1$=LP filter, and $f_2$=HP filter). In this example application of process 400, filtering was implemented only in the channel direction. FIG. 5 presents a graph 500 that plots the respective filters' frequency responses, and FIG. 6 presents example CT images before and after application of the trained NN to corresponding sinogram data in accordance with the preliminary testing of this set-up. All respective CT images shown in FIG. 6 were reconstructed from sinogram data using standard FBP reconstruction. Images 601A-D correspond to CT images of the chest and liver and images 602A-D correspond to CT images of the liver alone. Images 601A and 602A respectively correspond to CT images generated from the original, unprocessed (i.e., corrupted) sinogram data. Images 601B and 602B correspond to CT images generated from output sinogram data of a NN trained with only the LP filter (i.e., weighting factor $\alpha$=0). Images 601C and 602D correspond to CT images generated from output sinogram data of a NN trained with both the LP and HP filters with a weighting factor of $\alpha$=0.6, and images 601D and 602D correspond to CT images generated output sinogram data from a NN trained with both the LP and HP filters with a weighting factor of $\alpha$=0.8. As can be observed in FIG. 6, the fine-grain texture (i.e., high frequency components) in the reconstructed CT images generated from the NN corrected sinogram data (i.e., images 601B-D and images 602B-D) is significantly improved relative to the uncorrected images (i.e., images 601A and 602A). Furthermore, the fine-grain texture (i.e., high frequency components) in the reconstructed CT images increases as the weighting factor increases for the HP filter (e.g., $\alpha$>0) demonstrating the efficacy of application of both filters to improve the quality of the CT images.

Figures 7A, 7B:
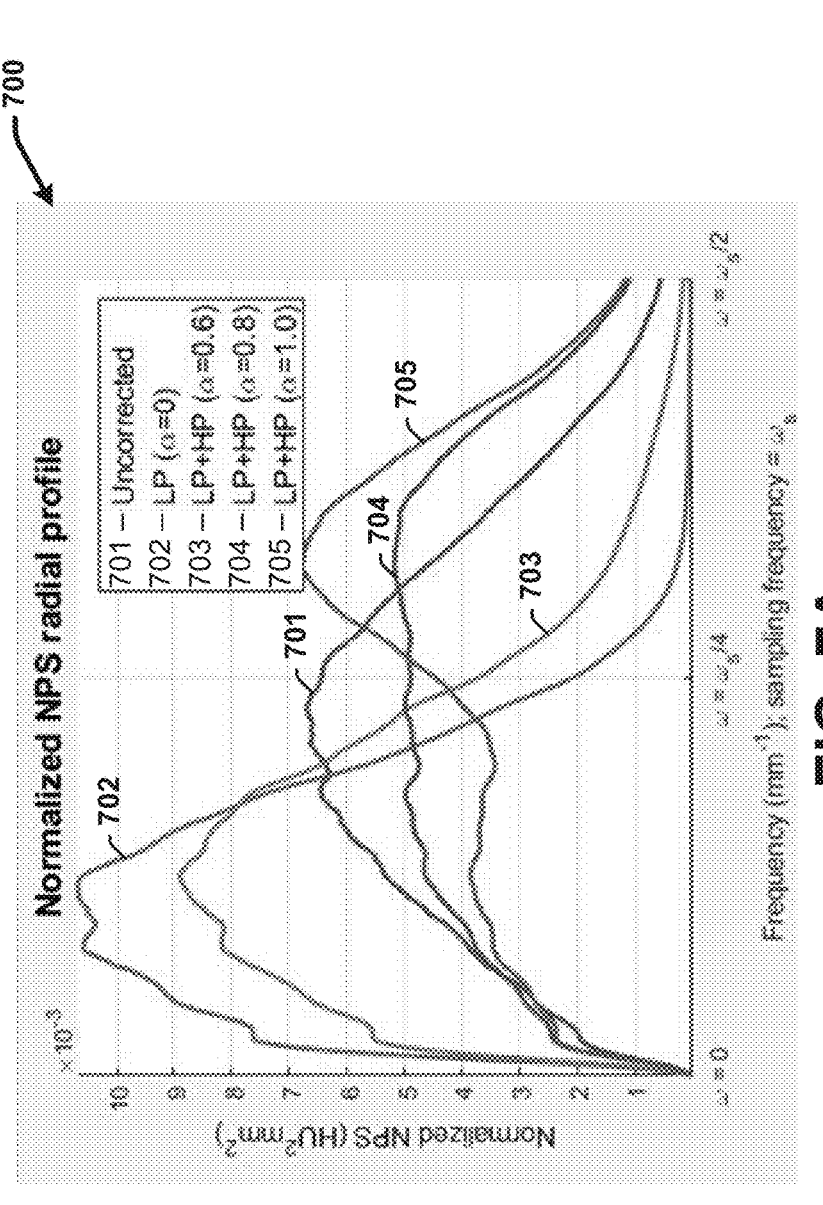
FIG. 7A presents a graph illustrating normalized noise power spectrum (NPS) curves computed from an assumed uniform liver region for an uncorrected image and different versions of losses.
FIG. 7B presents a table describing the entropy values of the NPS curves illustrated in the graph of FIG. 7A.

FIG. 7A presents a graph 700 illustrating normalized noise power spectrum (NPS) curves computed from CT images of the liver corresponding to images 602A-D and an additional CT image generated from output sinogram data of a NN trained with both the LP and HP filters with a weighting factor of $\alpha$=1.0. Each of the respective NPS curves 701-705 were computed from an assumed uniform liver region in the corresponding CT images. FIG. 7B presents a table 710 describing the entropy values of the NPS curves illustrated in the graph of FIG. 7A. The NPS resulting from the use of only LP filter in the loss function (i.e., NPS curve 702) can be seen to lack most of the high frequency content. Use of HP filter on the error between the input and the output brings some of the high frequency components back. In some embodiments, the value of the weighting factor $\alpha$ applied to the HP filter error content can be adjusted based on the balance between NPS and noise tolerance in the image.

To assess the flatness of the NPS curves, entropy measurements were performed in accordance with Equation 7.

$$\text{Entropy} = \sum_{\omega_i=0}^{\omega_i=\omega_s/2} nps(\omega_i)\log_2\left(\frac{1}{nps(\omega_i)}\right).$$ Equation 7

It can be seen in table 710 that entropy or flatness of the NPS curves increases with $\alpha$ as far as 0.8, but it suffers from excessive high frequency emphasis for $\alpha$ of 1.0. This case exhibits undesirable streaks in the image as well.

Figure 8:
FIG. 8 illustrates a high-level flow diagram of an example training process for training a NN to control removal of select features in accordance with one or more embodiments of the disclosed subject matter.

FIG. 8 illustrates a high-level flow diagram of another example training process for training a NN to control removal of select features in accordance with one or more embodiments of the disclosed subject matter. Process 800 is similar to process 400 with the exception of a feature extraction process at 810 in place of the second filtering step at 410. In this regard, processing steps 802, 804 and 806 respectively correspond processing steps 202, 204 and 206 described with reference to process 200, and processing step 808 can correspond to processing step 408 in process 400. Repetitive description of like elements employed in respective embodiment is omitted for sake of brevity.

In accordance with process 800, the feature extraction process at 810 can be used to remove select feature content from error content (Error$_2$) that represents the difference between the NN input data $Y_k$ and output data $g(Y_k)$. As applied to CT imaging, this feature extraction process can be used to selectively penalize removal of defined structures from input CT images (i.e., the image domain) such as specific anatomical features and structures (e.g., vessels, lesions, and other fine/high detailed structures) and/or in the sinogram domain.

In this regard, in many DL CT imaging applications, the goal may be suppression of photon counting noise that is approximately white. Training can be accomplished in the image domain using low-noise reconstructions as targets and either similar, lower-dose images, or the target image with realistic noise added as inputs. The network then learns to erase components with little spatial correlation and produces a smoother, lower-noise image. Application in the sinogram may use a similar training scheme to remove spatially uncorrelated noise.

Removal of high frequencies in denoising nearly invariably includes some edge resolution reduction and contrast reduction in fine structures. If the goal is to remove only spatially uncorrelated components, the residual between input and output of the NN should not present structured information, whose presence generally indicates attenuation of underlying signal of possible diagnostic importance. To help whiten the residual and regain edge and contrast information, in some embodiments, the feature extraction process performed at 810 comprises a process for the detection of classes of structured information in the residual, such that it can be penalized by the loss function at 816. An example of this issue, attacked in the image domain, is illustrated in 9.

Figure 9:
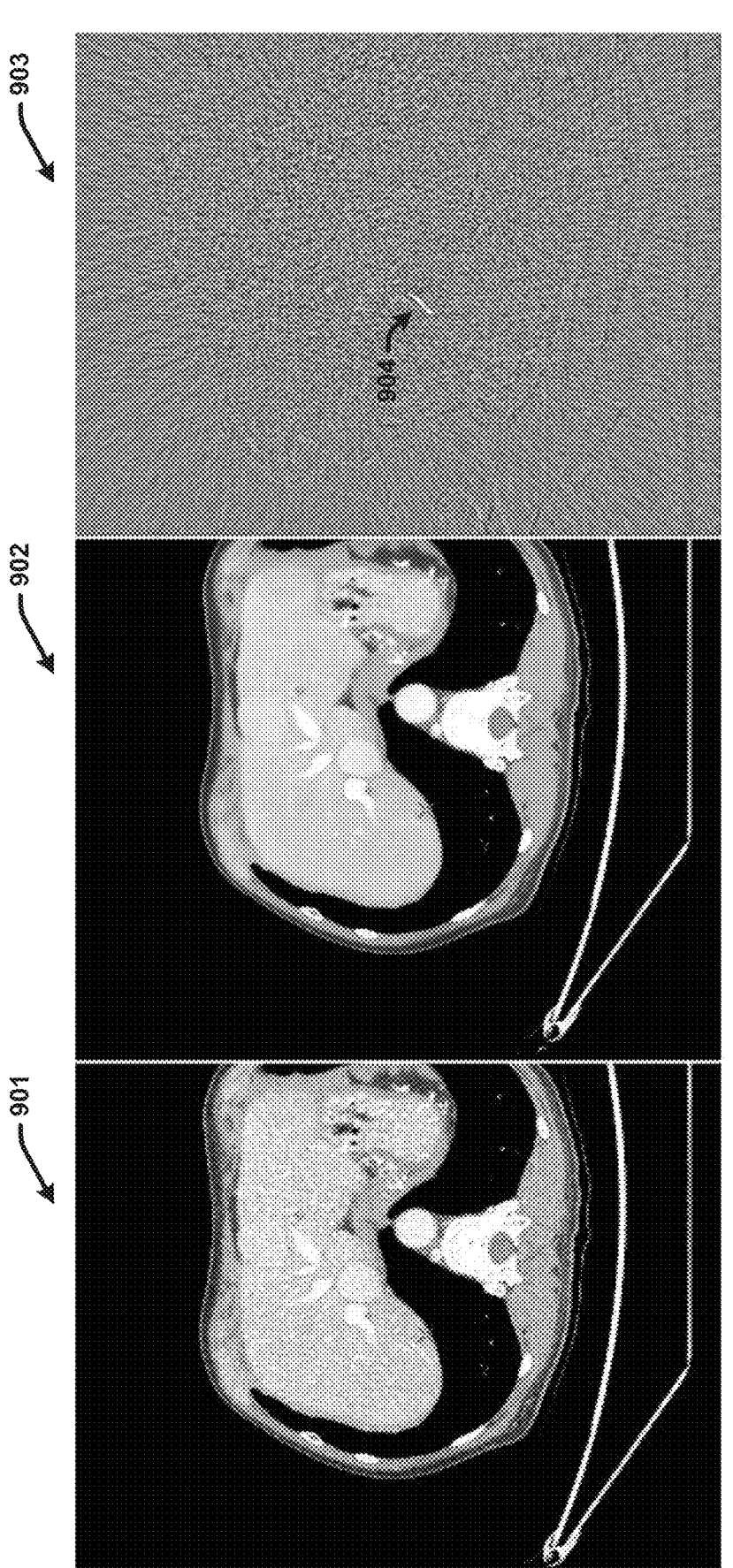
FIG. 9 presents an example input CT image, a denoised output version of the CT image, and a residual differential image between the input and output CT images.

In this regard, FIG. 9 presents an example original CT image 901, a DL generated denoised version 902 of the original CT image (i.e., the output image) and a residual image 903 that represents the difference between the input and output images. In accordance with this example, the denoised image 902 was generated from the CT image 901 via a NN designed to eliminate noise from soft tissue areas. While the signal-to-noise ratio is certainly improved in the denoised image 902, blood vessels (here containing contrast) are also attenuated. In the residual image 903, these structures are visible in contrast to the surrounding, spatially uncorrelated noise. One example of these structures corresponding to a blood vessel is indicated by arrow 904.

With reference to FIGS. 8 and 9, in one or more embodiments, the feature extraction process at 810 can comprise an image analysis process to isolate these types of structures in the residual image and penalize their presence in the residual as part of the DL loss function. The detection of these elements may be pursued by filtering the residual image for oriented edge detection and shape analysis of resulting connected components. The aspect ratio of the structure's components can also be used part of the feature detection and extraction process. Thus, in some embodiments, process 800 can correspond to process as 400, yet with replacement of the second filtering process ($f_2$) with feature extraction to emphasize the possibly greater complexity in extraction of residual elements whose removal could cause a compromise in diagnostic quality. This feature extraction process can exploit image analysis beyond the simple spectral separation described above. With these embodiments, the backpropagation of the loss at 816 may be implemented in parallel with a more generic denoising training, with the two gradients combined for adjustment of the NN (i.e., g or $g_\theta$). The filter $f_1$ applied at 806 may be all-pass for conventional denoising training.

In this regard, in one or more embodiments, the input data $Y_k$ processed by the NN in process 800 can comprise CT images (i.e., original/corrupted CT images). At 802, process 800 can comprise processing the input images to generate denoised versions thereof as output $g(Y_k)$. At 808, the training system (e.g., the computing system performing the training processes, an example of which is presented in FIG. 13) can compare the output image with the input image to generate the residual image (e.g., corresponding to residual image 903) based on the difference between the two. With these embodiments, $Error_2$ corresponds to the residual image. At 810, the system can perform a feature extraction processes to identify and extract (e.g., using feature extraction component 1214) one or more defined structures present in the residual image that the system operator/designer would like the NN to learn to retain in the output images and thus penalize their removal in the loss evaluation at 816.

The specific structural features that are extracted at 810 can vary and are configurable. For example, the specific structural features can vary depending on the anatomical region or regions represented in the input CT images (e.g., structures/features important for retaining may vary for the chest relative to the liver for instance) and the clinical application/context for usage of the output images. The mechanism employed by the feature extraction process at 810 to identify and detect the target structures in the residual image can also vary. For example, in various embodiments, the feature extraction process at 810 can comprise processing the residual image to detect defined anatomical features using image analysis tools (e.g., object detection software, anatomical object/organ segmentation models, etc.) configured to detect, classify and/or extract specific structures present in the residual images based on size, shape, relative spatial location, boundary/edge information, aspect ratio of the structure's components, and so on. In some embodiments, the feature extraction process at 810 can comprise generating segmentation masks corresponding to the identified target structural features in the residual image and applying the segmentation mask to the corresponding original input image to identity and extract these features from the original input image data.

The output of the feature extraction process at 810 can comprise information identifying or indicating the one or more features extracted from the residual image data. This information is represented in process 800 as $Error_{2feature}$ data. For example, in some implementations, the $Error_{2feature}$ data can comprise mask data corresponding to segmentation masks generated as overlay data onto the input image $Y_k$ and/or the output image $g(Y_k)$. In another implementation, the $Error_{2feature}$ data can comprise the extracted features from the input image (as correlated from the residual image) and re-inserted back into the output image with information (e.g., spatial masks) marking the boundary lines of the respective features in spatial correlation. In accordance with process 800, the $Error_{2feature}$ data may also be (optionally) weighted using a configurable weighting factor $\alpha$ at 812 to increase or decrease its penalty value in the loss function.

The right branch processing including the filtering using $f_1$ of process 800 can correspond to that described with reference to process 200 and/or comprise a different filtering process. In this regard, as applied in the image domain, the output data $g(Y_k)$ will comprise a denoised CT image and the target data $X_k$ will comprise one or more target "ideal" CT images. At 804, the system can compare the output image with the target image to determine error data ($Error_1$) that represents a difference in content between the respective images. At 806, the system can apply a filter $f_1$ configured to remove some select content from the error data that the system operator/designer does not want the network to penalize, resulting in filtered error content ($Error_{1f}$).

At 814 the first and second filtered error signals (e.g., ($Error_{1f}$ and $Error_{2feature}$ or $\alpha$ $Error_{2feature}$) can be aggregated or combined as input to the loss function computed at 816. In this regard, at 816, the loss is computed using a suitable loss function that determines and applies a penalty (i.e., computes the loss) based on the aggregated filtered error content. The specific loss function L used at 816 can include MSE, absolute MSE, Equation 4, Equations 5 and 6, combinations thereof, or another type of loss function. At 818, the system (e.g., the computing system performing the training processes, an example of which is presented in FIG. 13) further determines the gradients based on the loss and adjusts the NN accordingly.

Figure 10:
FIG. 10 presents an example feature extraction process for CT images in accordance with one or more embodiments of the disclosed subject matter.

FIG. 10 presents an example feature extraction process 1000 for CT images in accordance with one or more embodiments of the disclosed subject matter. In some embodiments, the feature extraction process at 810 in process 800 can comprise one or more aspects of feature extraction process 1000. Process 1000 is exemplified in association with detecting vessel-like structures in the residual image, which are important features for retaining in NN corrected liver CT images. In accordance with feature extraction process 1000, image 1004 corresponds to the original input image processed by the DL NN, and image 1002 corresponds to the residual image that is the difference between the input image 1002 and the DL NN output image (not shown). At 1006, a Log operation is performed to process the input image 1004 and the residual image 1002 in accordance with conventional Laplacian or Gaussian processing to detect certain types of edges in the respective images. Further image analysis processing is performed on the residual image in the three-capture dimensions (e.g., axial plane at 1008, sagittal plane at 1010 and coronal plane at 1012). The image analysis and feature extraction processing performed in the respective planes can employ same or different techniques and thresholds. For example, as illustrated with refence to the axial plane, the image analysis can comprise evaluating the residual image with respect to object shape, size, aspect ratio, number of pixels and the like to identify distinct features that satisfy defined criteria for the features. In some embodiments, the image analysis performed at 1008, 1010 and 1012 can result in the generation of object masks generated as overlay data positioned relative to the residual image 1002. At 1014A, a shape/size filtering process can be applied to remove any identified features that do not satisfy defined shape and/or size criteria for the target structures (e.g., maximum and/or minimum length criteria, maximum and/or minimum diameter criteria, etc.) in the axial plane. A same or similar filtering process can be performed for the sagittal plane (at 1014S) and the coronal plane (at 1014C). At 1016, the system can generate a final mask over 1016 the residual image that comprises the identified features to be retained from the input image 1004 in the NN output image. With reference again to FIG. 8, in some embodiments, the feature extraction process at 810 in process 800 can end here with the generation of such a final mask applied to the residual image. With these embodiments, the residual image with the final mask can correspond to the $\text{Error}_{2feature}$ data in process 800 that is penalized by the Loss function at 816.

Process 1000 includes a blending step at 1016, which involves blending the identified features back into the NN output image to generate a blended image 1020. The blended image 1020 corresponds to the desired final image that the NN in process 800 can be trained to generate when incorporating the feature extraction and perseveration analysis into the loss function as illustrated in FIG. 8. In some embodiments, the entirety of process 1000 (including the blending step) can be applied as a NN post-processing mechanism. With these embodiments, the feature extraction and reintroduction thereof back into the NN output image would not be incorporated into the loss analysis as illustrated in FIG. 8. However, by including the feature extraction and structure preservation in the Loss during NN training, the disclosed techniques significantly reduce processing time at the inferencing phase.

Figure 11:
FIG. 11 presents example CT images in association with performing structure preservation correction using NN processing in accordance with one or more embodiments of the disclosed subject matter.

FIG. 11 presents example CT images in association with performing structure preservation correction using NN processing in accordance process 1000. Image 1101 corresponds to a DL NN input CT image, image 1102 presents the DL NN output image, a denoised image. Image 1103 presents the mask over the input image 1101 corresponding to the identified features to be retained from the input image and image 1104 comprises a blended version of the output image 1102 with the masked features extracted from the input image and reinserted back into the DL output image. Some of the blood vessels with reduced contrast in the DL output appear brighter in the final corrected image 1104. In this example, the structure preservation was performed as a post-processing step.

Figure 12:
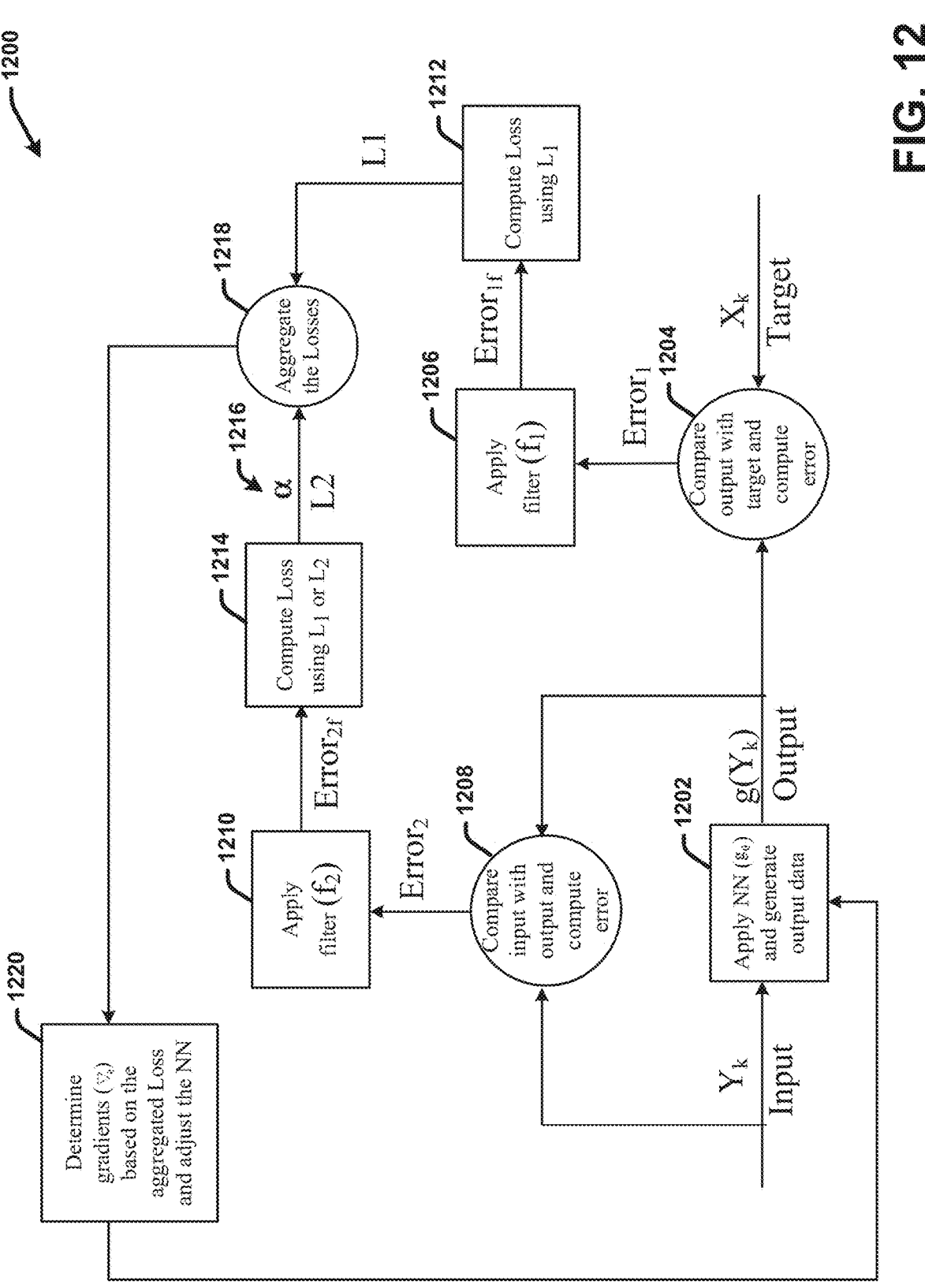
FIG. 12 illustrates a high-level flow diagram of another example training process for training a NN to control error content using both filtering of the difference between the training input data and output data, and filtering of the difference between target and output, in accordance with one or more embodiments of the disclosed subject matter.

FIG. 12 illustrates a high-level flow diagram of another example training process 1200 for training a NN to control error content using both filtering of the difference between the training input data and output data, and filtering of the difference between target and output, in accordance with one or more embodiments of the disclosed subject matter. Process 1200 is similar to process 400 with the modification of separately evaluating the different branched error content (e.g., $\text{Error}_{1f}$ and $\text{Error}_{2f}$ respectively) with separate loss functions to determine two separate loss values based on the respective error content. The loss functions can be the same or different. These losses are then combined/aggregated and the gradients for adjusting the NN are determined based on the aggregated loss. In this regard, processing steps 1202, 1204, 1206, 1208 and 1210 respectively correspond processing steps 402, 404, 408, 406 and 410 described with reference to process 400. Repetitive description of like elements employed in respective embodiment is omitted for sake of brevity.

In accordance with process 1200, at 1212, the first filtered error content ($\text{Error}_{1f}$) can be processed as input to a first lost function ($L_1$) to compute a first loss value (L1) based on the first filtered error content. At 1212, the second filtered error content ($\text{Error}_{2f}$) can be processed using the first lost function ($L_1$) or a second loss function ($L_2$) to compute a second loss value (L1) based on the second filtered error content. In this regard, in some embodiments, the same loss function can be applied to $\text{Error}_{1f}$ and $\text{Error}_{1f}$. In other embodiments, the respective loss functions can be different and specifically tailored to the type of error content being evaluated. For example, in implementations in which $f_1$ and $f_2$ respectively filter the error content as function of different frequencies or frequency ranges (e.g., LP and HP respectively), the respective loss functions $L_1$ and $L_2$ can respectively be tailored to the corresponding part of the frequency spectrum. At 1216, the second loss value (L2) may (optionally) be weighted before aggregation with the first loss value (L1) at 1218. At 1220, the gradient is then computed based on the aggregated loss (i.e., sum of those two losses) in question in each branch and the NN is adjusted accordingly.

Figure 13:
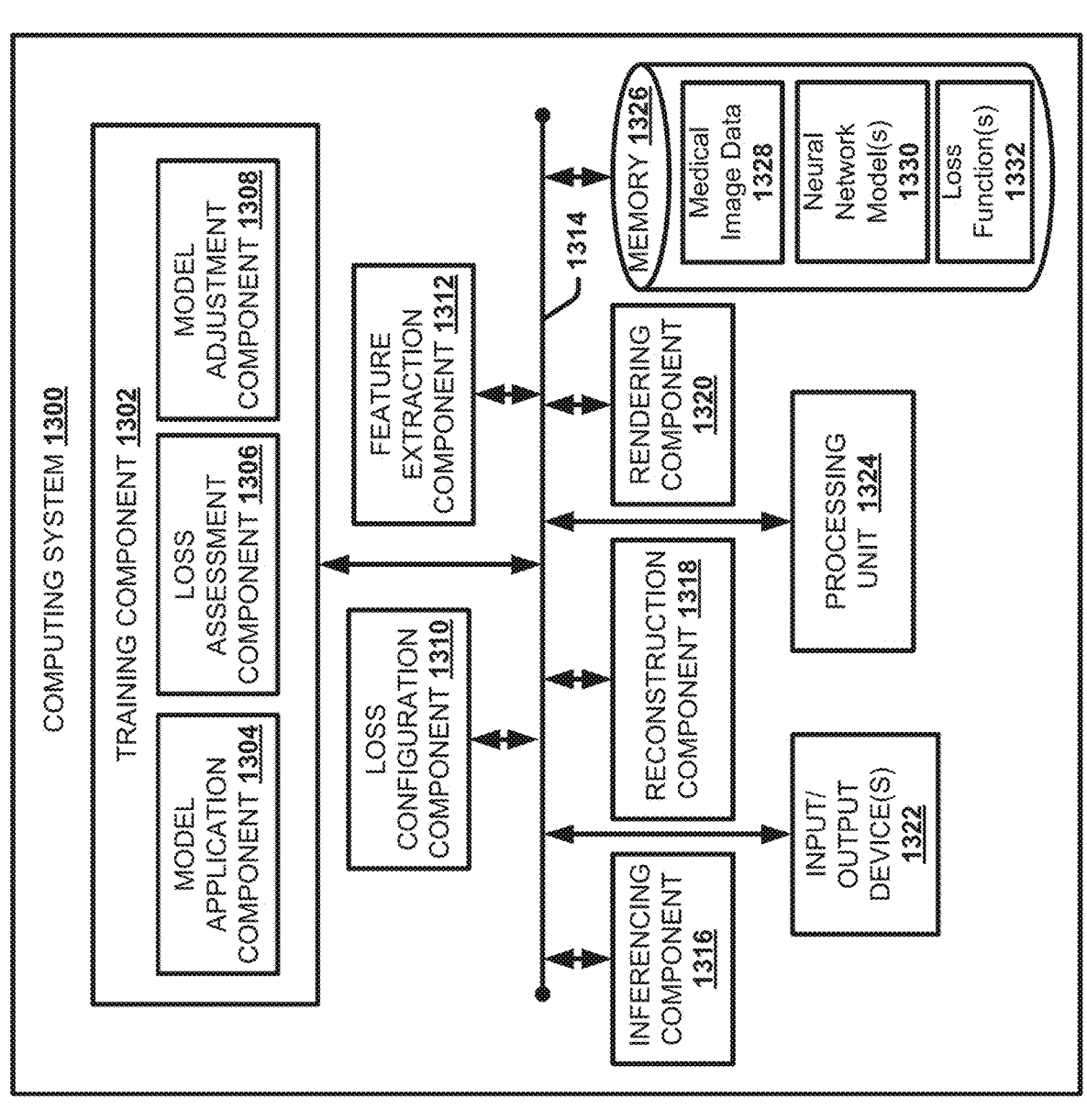
FIG. 13 illustrates a block diagram of an example, non-limiting computing system that facilitates generating neural networks tailored to optimize specific medical image properties using novel loss functions in accordance with one or more embodiments of the disclosed subject matter.

FIG. 13 illustrates a block diagram of an example, non-limiting computing system 1300 that facilitates generating neural networks tailored to optimize specific medical image properties using novel loss functions in accordance with one or more embodiments of the disclosed subject matter. Computing system 1200 can comprise software, hardware or a combination thereof that is configured to perform the NN training processes and associated image processing functions described herein with reference to FIGS. 1-12 and FIG. 13. Computing system 1300 can further provide for applying the trained NNs to new data (i.e., new input images and/or sinogram data) to generate optimized/corrected output data, generating reconstructed, optimized CT images using optimized sinogram data, and rendering the reconstructed CT images, among other related tasks.

Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

As used herein, the one or more machines can be and/or can include one or more of a computing device, a general-purpose computer, a special-purpose computer, a quantum computing device (e.g., a quantum computer), a tablet computing device, a handheld device, a server class computing machine and/or database, a laptop computer, a notebook computer, a desktop computer, a cell phone, a smart phone, a consumer appliance and/or instrumentation, an industrial and/or commercial device, a digital assistant, a multimedia Internet-enabled phone and/or another type of device. Computing system 100 can also be or correspond to one or more real or virtual (e.g., cloud-based) computing devices.

In this regard, computing system 1300 includes training component 1302, loss configuration component 1310, feature extraction component 1312, inferencing component 1316, reconstruction component 1318 and rendering component 1320, all of which can be or include machine-executable components embodied within one or more machines (e.g., embodied in one or more computer-readable storage media associated with one or more machines), which when executed by the one or more machines (e.g., processors, computers, computing devices, virtual machines, etc.) can cause the one or more machines to perform the operations described. For example, system 100 can be any suitable machine that can execute one or more of the operations described with reference to the training component 1302, the loss configuration component 1310, the feature extraction component 1312, the inferencing component 1316, the reconstruction component 1318, the rendering component 1320, and other components described herein.

These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 1326 of the computing system 1300 which can be coupled to processing unit 1324 for execution thereof. Examples of said memory and processing unit well as other suitable computer or computing-based elements (e.g., input/output devices 1320 for example), can be found with reference to FIG. 14, and can be used in connection with implementing one or more of the systems or components shown and described in connection with FIG. 1 or other figures disclosed herein.

The memory 1326 can further store medical image data 1328, one or more neural network (NN) models 1330 and one or more loss functions 1332. The one or more NN models 1330 can correspond to both pre-trained and trained versions of NN that are trained by the training component 1302 to perform optimization of medical image data using the training processes described herein, including process 100, process 200, process 400, process 800 and/or variations thereof. For example, the NN models can comprise the NN (i.e., g or g$_\theta$) described with refence to process 100, process 200, process 400, process 800 and/or variations thereof. In this regard, the one or more NN models 1330 can comprise different versions of the same model yet trained with different loss functions, trained with different processes (i.e., of process 100, 200, 400, 800 or combinations thereof), trained with different values for the weighting factor α, trained with different filters and/or filter weights for f$_1$ and/or f$_2$, and/or trained with different input data (e.g., different types of input medical images and/or corresponding sinogram data).

The training component 1302 can perform the NN model training processes described herein (i.e., of processes 100, 200, 400, 800, 1200 or combinations thereof) to generate the trained versions of the NN models. To facilitate this end, the training component 1302 can include model application component 1304, loss assessment component 1306 and model adjustment component 1308. These components can respectively be configured to perform one or more processing steps of the training processes. For example, in some embodiments, the model application component 1304 can apply the NN to the input training data $Y_k$ to generate the output data $g(Y_k)$. The loss assessment component 1306 can generate the error content or error signals (i.e., (e.g., Error$_{1f}$, Error$_{2f}$ or αError$_{2f}$, Error$_{2feature}$, etc.) for processing by the loss function. The loss assessment component 1306 can further apply the loss function to the one or more error signals to compute the loss (e.g., at 106 in process 100, 208 in process 200, 416 in process 400, and 816 in process 800). In embodiments in which the feature extraction process is performed during model training to assess the loss penalty, the feature extraction component 1312 can perform the feature extraction process during model training to generate the Error$_{2feature}$ content, as described with reference to FIGS. 8-12. The model adjustment component 1308 can further determine how to adjust the NN model gradients (e.g., NN node weights/coefficients, interconnections, and other parameters controlling how the network operates on the input data) based on the loss and update the NN model accordingly (e.g., processing step 108 in process 100, processing step 210 in process 200, processing step 418 in process 400 and processing step 818 in process 800).

As described above, the optimization task that the NN models 1330 are trained to perform can relate to improving one or more specific features or components of medical images by processing the medical images and/or raw signal data used to generate the medical images as input (e.g., sinogram data, photon projection data, etc.). As described above, in some embodiments, the specific features or components can comprise a spatial frequency component (i.e., training the NN to control frequency content of the error), a spatial feature component (i.e., training the NN to control spatial feature variables), combinations thereof, and other components of the error content. In some implementations, the one or more NN models 1330 may also be configured to process a variety of additional metadata associated with the input medical image data in association with performing optimization thereof (e.g., metadata regarding acquisition parameters/protocols used, acquisition position/orientation information, anatomical region depicted, patient information, and so on). Generally, the one or more NN models 1330 comprise artificial neural networks (ANNs) that employ a deep learning architecture. The type of the ANNs can vary and can include but are not limited to, deep neural networks (DNNs), deep belief networks, deep reinforcement learning networks, recurrent neural networks, convolutional neural networks (CNNs), and the like.

The loss functions 1332 can correspond to the various novel loss functions described below that are used by the training component 1302 to train the one or more NN models 1330 to perform the operations described. In this regard, with reference to processes 100, 200, 400 and 800, the loss functions 1332 can correspond to the respective loss functions L that are applied at 106 in process 100, 208 in process 200, 416 in process 400, and 816 in process 800. For example, the loss functions 1332 may comprise loss functions represented by Equations 2-6. As described above, these loss functions can be configured to process one or more different input signals corresponding to error content that has been processed using the techniques described with reference to process 200, 400, 800, 1200 or a combination thereof. For example, in some embodiments, the loss function input signals can comprise error content corresponding to the difference between the NN input and the target data set that has been filtered using f$_1$ (i.e., Error$_{1f}$), which in some embodiments can comprise a spatial frequency filter that filters the error content based on one or more first frequency components of the error content (e.g., as described with reference to process 200). Additionally, or alternatively, the loss function input signals can comprise error content corresponding to the difference between the NN input data and output that has been filtered (and optionally weighted by weighting factor α) using f$_2$ (i.e., Error$_{2f}$ or αError$_{2f}$), which in some embodiments can comprise another spatial frequency filter that filters the error content based on one or more second frequency components of the error content (e.g., as described with reference to process 400). Additionally, or alternatively, the loss function input signals can comprise error content corresponding to the difference between the NN input data and output data that has been processed using feature extraction to identify, extract and re-apply select structural features to the error content (i.e., in the form of feature mask data or the like) desired for retaining from the input image data ((i.e., Error$_{2feature}$ or αError$_{2feature}$), as described with reference to process 800.

Additionally, or alternatively, the system can employ two separate loss functions to separately determine different loss values based on different filtered error content, and thereafter aggregate the losses, as described with reference to process 1200.

Still in other embodiments, the loss function input signals may comprise a composite of differences among all three (or more) of these different types of error signals (e.g., $Error_{1f}$+$Error_{2f}$ or $\alpha Error_{2f}$+$Error_{2feature}$) to assess the training penalty. Additionally, or alternatively, the loss function can use a composite of differences among three or more signals as input to the training penalty, wherein the three or more signals are not limited to "Error" signals such as those described herein. For example, the loss function can correspond to Equation 2, wherein the loss function has three arguments. These three arguments are not limited to "Error" signals and can exploit any relationship among the input signals.

The medical image data 1328 can include the medical image data and associated metadata that is processed by the NN models 1328 and in some implementations, the reconstruction component 1318. For example, in some embodiments in which the NN model 1330 process CT sinogram data (e.g., as opposed to actual CT images), the reconstruction component 1318 can process the corrected/optimized sinogram data using one or more conventional CT image reconstruction methods (e.g., FBP or the like) to generate reconstructed, optimized CT images (e.g., that can be rendered/displayed) using the corrected/optimized sinogram data. In this regard, the medical image data 1328 can include the training data (e.g., including the target data or target dataset) as well as the runtime processing data that is processed by the trained models by the inferencing component 1316 during the inferencing phase (i.e., new unseen data). In this regard, once trained, the inferencing component 1316 can apply the trained versions of the NN models 1330 to new input data in inferencing mode to generate optimized output data (i.e., corrected sinogram data and/or denoised/optimized CT images). The medical image data 1328 can also include the optimized or reconstructed medical image data (i.e., the NN output data) generated by system during training and/or inferencing mode. Additionally, or alternatively, any medical image data processed and/or generated by the computing system 1300 may be stored at another suitable network accessible location, provided to the computing system 1300 via another system or device (e.g., directly from the medical image data capturing system) or the like. In various embodiments, the type of the medical image data 1328 comprises CT data (e.g., CT images and/or raw CT image sinogram data). However, the disclosed techniques are not limited to CT and may be extended to other imaging modalities.

Computing system 1300 can further include one or more input/output devices 1322 that provide for receiving user input in association with performing the operations described and/or rendering information to one or more users. For example, in some embodiments, information processed by the computing system 1300 (e.g., medical image data pre and/or post neural network processing and reconstruction) can be presented or rendered to a user via a suitable display (i.e., the input/output devices 1322 can include a display) using rendering component 1320. With these embodiments, the computing system 1300 can correspond to a computing device employed by a user (e.g., a clinician, a radiologist, a technician, a machine learning (ML) model developer, or the like) to interface with one or more features and functionalities provided by the respective components of the computing system 1300. The one or more input/output device 130 can also provide for receiving user input selecting and/or configuring (e.g., via the loss configuration component 1312) the specific features and functionalities of the loss functions 1332 and/or the specific loss functions to be applied during model training. In this regard, as discussed above, the specific loss functions that may be used during NN training, the specific thresholds of the loss functions (e.g., controlling the specific frequency or frequency ranges for filtering the error content by $f_1$ and/or $f_2$ for example), the value of the weighting factor $\alpha$ and/or the specific features for retaining via the feature extraction component 1314 are configurable and can be selected/configured by the system operator/designer (i.e., a model developer, a radiologist, etc.). The loss configuration component 1312 can provide for selecting/configuring one or more of these variables/parameters evaluated by the loss function in association with model training. System 100 can further include a system bus 1314 that communicatively and operatively couples the various components and devices of the computing system to one another.

FIG. 14 illustrates a block diagram of an example, non-limiting computer implemented method 1400 for CT image reconstruction that employs a NN to control error localized in frequency and/or spatial content in accordance with one or more embodiments of the disclosed subject matter. Repetitive description of like elements employed in respective embodiment is omitted for sake of brevity.

Method 1400 comprises, at 1402 training, by a system comprising a processor (e.g., system 1300 using training component 1302) a neural network (e.g., one or more neural network models 1330) to generate a modified version of computed tomography data comprising one or more optimized properties relative to the computed tomography data using a loss evaluation mechanism (e.g., one or more loss functions 1332 and the loss calculation and gradient updating mechanisms described with reference to process 200, 400, 800 or 1200) tailored to control learning adaptation of the neural network based on error attributed to one or more defined components associated with the computed tomography data, resulting in a trained neural network, wherein the one or more defined components comprise at least one of a spatial frequency component or a spatial feature component. At 1404, method 1400 further comprises applying, by the system, the trained neural network to new computed tomography data to generate a new modified version of the new computed tomography data comprising the one or more optimized properties (e.g., via inferencing component 1316).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 15, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 15:
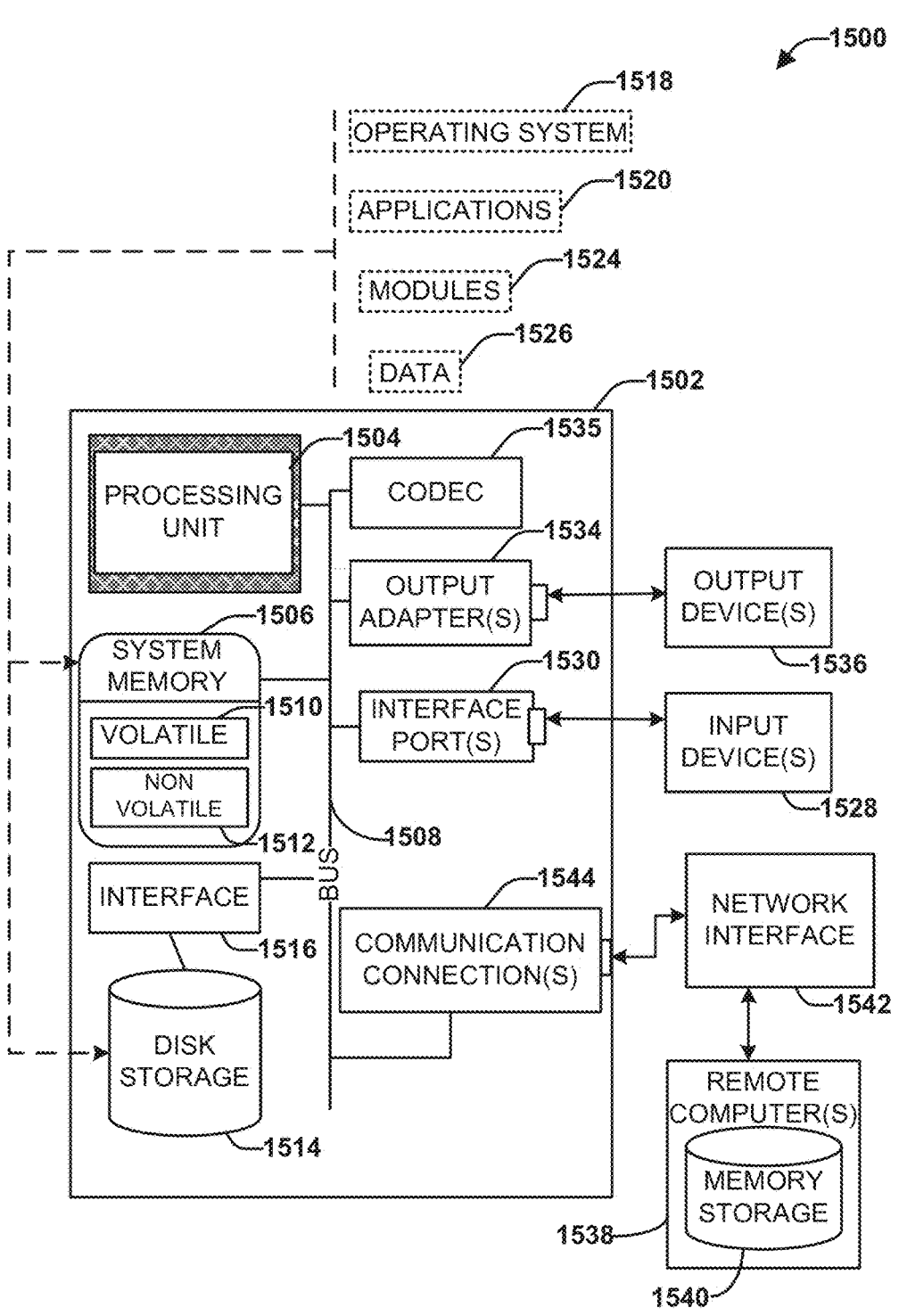
FIG. 15 illustrates a block diagram of an example, non-limiting operating environment in which one or more embodiments described herein can be facilitated.

With reference to FIG. 15, an example environment 1500 for implementing various aspects of the claimed subject matter includes a computer 1502. The computer 1502 includes a processing unit 1504, a system memory 1506, a codec 1535, and a system bus 1508. The system bus 1508 couples system components including, but not limited to, the system memory 1506 to the processing unit 1504. The processing unit 1504 can be any of various available processors. Dual microprocessors and other multiprocessor architectures also can be employed as the processing unit 1504.

The system bus 1508 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13164), and Small Computer Systems Interface (SCSI).

The system memory 1506 includes volatile memory 1510 and non-volatile memory 1512, which can employ one or more of the disclosed memory architectures, in various embodiments. The basic input/output system (BIOS), containing the basic routines to transfer information between elements within the computer 1502, such as during start-up, is stored in non-volatile memory 1512. In addition, according to present innovations, codec 1535 can include at least one of an encoder or decoder, wherein the at least one of an encoder or decoder can consist of hardware, software, or a combination of hardware and software. Although, codec 1535 is depicted as a separate component, codec 1535 can be contained within non-volatile memory 1512. By way of illustration, and not limitation, non-volatile memory 1512 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1512 can employ one or more of the disclosed memory devices, in at least some embodiments. Moreover, non-volatile memory 1512 can be computer memory (e.g., physically integrated with computer 1502 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1510 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1502 can also include removable/non-removable, volatile/non-volatile computer storage medium. FIG. 15 illustrates, for example, disk storage 1514. Disk storage 1514 includes, but is not limited to, devices such as a magnetic disk drive, solid state disk (SSD), flash memory card, or memory stick. In addition, disk storage 1514 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1514 to the system bus 1508, a removable or non-removable interface is typically used, such as interface 1516. It is appreciated that disk storage 1514 can store information related to an entity. Such information might be stored at or provided to a server or to an application running on an entity device. In one embodiment, the entity can be notified (e.g., by way of output device(s) 1536) of the types of information that are stored to disk storage 1514 or transmitted to the server or application. The entity can be provided the opportunity to opt-in or opt-out of having such information collected or shared with the server or application (e.g., by way of input from input device(s) 1528).

It is to be appreciated that FIG. 15 describes software that acts as an intermediary between entities and the basic computer resources described in the suitable operating environment 1500. Such software includes an operating system 1518. Operating system 1518, which can be stored on disk storage 1514, acts to control and allocate resources of the computer system 1502. Applications 1520 take advantage of the management of resources by operating system 1518 through program modules 1524, and program data 1526, such as the boot/shutdown transaction table and the like, stored either in system memory 1506 or on disk storage 1514. It is to be appreciated that the claimed subject matter can be implemented with various operating systems or combinations of operating systems.

An entity enters commands or information into the computer 1502 through input device(s) 1528. Input devices 1528 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1504 through the system bus 1508 via interface port(s) 1530. Interface port(s) 1530 include, for example, a serial port, a parallel port, a game port, and a universal serial bus (USB). Output device(s) 1536 use some of the same type of ports as input device(s) 1528. Thus, for example, a USB port can be used to provide input to computer 1502 and to output information from computer 1502 to an output device 1536. Output adapter 1534 is provided to illustrate that there are some output devices 1536 such as monitors, speakers, and printers, among other output devices 1536, which require special adapters. The output adapters 1534 include, by way of illustration and not limitation, video and sound cards that provide a means of connection between the output device 1536 and the system bus 1508. It should be noted that other devices or systems of devices provide both input and output capabilities such as remote computer(s) 1538.

Computer 1502 can operate in a networked environment using logical connections to one or more remote computers, such as remote computer(s) 1538. The remote computer(s) 1538 can be a personal computer, a server, a router, a network PC, a workstation, a microprocessor based appliance, a peer device, a smart phone, a tablet, or other network node, and typically includes many of the elements described relative to computer 1502. For purposes of brevity, only a memory storage device 1540 is illustrated with remote computer(s) 1538. Remote computer(s) 1538 is logically connected to computer 1502 through a network interface 1542 and then connected via communication connection(s) 1544. Network interface 1542 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1544 refers to the hardware/software employed to connect the network interface 1542 to the bus 1508. While communication connection 1544 is shown for illustrative clarity inside computer 1502, it can also be external to computer 1502. The hardware/software necessary for connection to the network interface

1542 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
    a training component that trains a neural network to generate a modified version of computed tomography data comprising one or more optimized properties relative to the computed tomography data using a loss function tailored to control learning adaptation of the neural network based on error attributed to one or more defined components associated with the computed tomography data, resulting in a trained neural network.

2. The system of claim 1, wherein the one or more defined components comprise at least one of a frequency component, a visual feature component, or a spatial feature component.

3. The system of claim 1, wherein the computed tomography data comprises sinogram data for a computed tomography image and the modified version comprises modified sinogram data for the computed tomography image.

4. The system of claim 1, wherein the computed tomography data comprise a computed tomography image and the modified version comprises a reconstructed computed tomography image.

5. The system of claim 1, wherein the computer executable components further comprise:
an inferencing component that applies the trained neural network to new computed tomography data to generate a new modified version of the new computed tomography data exhibiting the one or more optimized properties.

6. The system of claim 5, wherein the computed tomography data comprises sinogram data for a computed tomography image, the modified version comprises modified sinogram data for the computed tomography image, the new computed tomography data comprises new sinogram data for a new computed tomography image, the new modified version comprises new modified sinogram data for the new computed tomography image, and wherein the computer executable components further comprise:
a reconstruction component that generates a reconstructed version of the new computed tomography image using the new modified sinogram data.

7. The system of claim 1, wherein the one or more defined components comprise a frequency component and wherein the loss function weights the error of as a function of the frequency component.

8. The system of claim 7, wherein the loss function penalizes removal of defined frequencies or frequency ranges, and wherein the defined frequencies or frequency ranges are adjustable.

9. The system of claim 1, wherein the loss function utilizes spatial filtering of a difference between output data of the neural network and a target data set as input to the loss function.

10. The system of claim 1, wherein the loss function applies a penalty to a difference between input data and output data of the neural network.

11. The system of claim 10, wherein the loss function assesses the penalty after spatial filtering of the difference.

12. The system of claim 9, wherein the one or more defined components comprise a spatial feature component and wherein the training component uses a spatial feature extraction step to furnish a mask to assess the penalty on the difference.

13. A system of claim 1, wherein the loss function uses a composite of differences among three or more signals as input to generate a training penalty.

14. A method, comprising:
training, by a system comprising a processor, a neural network to generate a reconstructed version of a computed tomography image comprising one or more optimized properties relative to the computed tomography image using a loss function tailored to control error in output data of the neural network based on a defined subset of variables associated with the computed tomography data; and
generating, by the system, a trained neural network model as a result of the training.

15. The method of claim 14, wherein the defined subset comprises at least one of, a frequency component, a visual feature component, or a spatial feature component.

16. The method of claim 14, wherein the computed tomography data comprises sinogram data for a computed tomography image and the modified version comprises modified sinogram data for the computed tomography image.

17. The method of claim 14, wherein the computed tomography data comprises a computed tomography image and the modified version comprises a reconstructed computed tomography image.

18. The method of claim 14, further comprising:
applying, by the system, the trained neural network to new computed tomography data to generate a new modified version of the new computed tomography data exhibiting the one or more optimized properties.

19. The method of claim 17, wherein the computed tomography data comprises sinogram data for a computed tomography image, the modified version comprises modified sinogram data for the computed tomography image, the new computed tomography data comprises new sinogram data for a new computed tomography image, the new modified version comprises new modified sinogram data for the new computed tomography image, and wherein the method further comprises:

generating, by the system, generates a reconstructed version of the new computed tomography image using the new modified sinogram data.

20. The method of claim 14, wherein the defined subset comprises a frequency variable and wherein the loss function weights the error of as a function of the frequency variable.

21. The method of claim 14, wherein the loss function utilizes spatial filtering of a difference between output data of the neural network and a target data set as input to the loss function.

22. The method of claim 14, wherein the loss function applies a penalty to a difference between input data and output data of the neural network.

23. The method of claim 22, wherein the loss function assesses the penalty after spatial filtering of the difference.

24. The method of claim 22, wherein the defined subset comprises a spatial feature component, and wherein the training comprises, performing, by the system, a spatial feature extraction step to furnish a mask to assess the penalty on the difference.

25. A non-transitory machine-readable storage medium, comprising executable instructions that, when executed by a processor, facilitate performance of operations, comprising:

training a neural network to generate a reconstructed version of a computed tomography image comprising one or more optimized properties relative to the computed tomography image using a loss function tailored to control error in output data of the neural network based on one or more defined components, the one or more defined components comprising at least one of a frequency component or a spatial feature component; and generating a trained neural network model as a result of the training.

\* \* \* \* \*